(12) United States Patent
Buschke

(10) Patent No.: US 6,306,086 B1
(45) Date of Patent: Oct. 23, 2001

(54) MEMORY TESTS USING ITEM-SPECIFIC WEIGHTED MEMORY MEASUREMENTS AND USES THEREOF

(75) Inventor: Herman Buschke, New York, NY (US)

(73) Assignee: Albert Einstein College of Medicine of Yeshiva University, Bronx, NY (US)

(*) Notice: Subject to any disclaimer, the term of this patent is extended or adjusted under 35 U.S.C. 154(b) by 0 days.

(21) Appl. No.: 09/369,651

(22) Filed: Aug. 6, 1999

(51) Int. Cl.[7] .............................. A61B 5/00; G09B 19/00; G09B 25/00
(52) U.S. Cl. ...................... 600/300; 128/898; 273/273; 273/459; 434/236; 434/365
(58) Field of Search .................... 600/300–301, 600/544–545; 434/236–238, 365; 128/898; 273/273, 459–460

(56) References Cited

U.S. PATENT DOCUMENTS 4,770,636 * 9/1988 Buschke ................................ 434/236
5,230,629 * 7/1993 Buschke ................................ 434/236
5,411,271 * 5/1995 Mirando ................................ 273/434

OTHER PUBLICATIONS

Buschke, et al. (1968) Journal of Experimental Psychology, 78, 502–509.
Deese, et al. (1957) Journal of Experimental Psychology, 54, 180–197.
Gianotti et al. (1994) Journal of Clinical and Experimental Neuropsychology, 16, 65–78.
Gibson, A.J. (1981) British Journal of Clinical Psychology, 20, 179–185.
Miller, E. (1971) Neuropsychologia, 9, 75–78.
Murdock, B.B., Jr. (1960) Journal of Experimental Psychology, 60, 222–234.
Murdock, B.B., Jr. (1962) Journal of Experimental Psychology, 64, 482–488.
Murdock, B.B., Jr. (1968) Journal of Experimental Psychology Monograph Supplement, Part 2, 76, 1–15.
Buschke, H. (1974) Science, 184, 579–581.
Buschke, et al. (1974) Neurology, 24, 1019–1025.
Buschke, et al. (1986) Developmental Neuropsychology, 2, 287–307.
Grober, et al. (1987) Developmental Neuropsychology, 3, 13–36.
Grober, et al. (1988) Neurology, 38, 900–903.
Grober, et al. (1992) Journal of Clinical and Experimental Neuropsychology, 14, 298–316.
Buschke, et al. (1997) Neurology, 48, 989–997.
Buschke, et al. (1999) Neurology, 52, 231–238.
Sliwinski, et al. (1997) Journal of International Neuropsychological Society, 3, 317–326.

(List continued on next page.)

Primary Examiner—Eric F. Winakur
Assistant Examiner—Michael C Astorino
(74) Attorney, Agent, or Firm—Amster, Rothstein & Ebenstein

(57) ABSTRACT

This invention relates to a method for increasing the usefulness, sensitivity and specificity of tests that measure memory and facets of memory, including learning, retention, recall and/or recognition. Specifically, the sensitivity and specificity of such tests are enhanced by selectively weighting the value of specific items recalled by the test subject, either by weighting such items within any specific testing trial or across numerous testing trials. Also disclosed are various methods of reducing ceiling effects in memory tests. The invention also provides improved tests which employ item-specific weighting for the diagnosis of Alzheimer's Disease and other dementia characterized by memory impairment, as well as a method of screening for and evaluating the efficacy of potential therapeutics directed to the treatment of such dementia.

19 Claims, 3 Drawing Sheets

OTHER PUBLICATIONS

Tounsi, et al. Alzheimer Disease and Associated Disorders, 13, 38–46.

Slamecka, et al. (1983) Journal of Experimental Psychology: Learning, Memory, and Cognition, 9, 384–397.

Buschke, H. (1984) Control of Cognitive Processing. In N. Butters, et al. (1986) p. 33–40.

Cullum, et al. (1993) Journal of Clinical and Experimental Neuropsychology, 15, 321–329.

McKhann, et al. (1984) Neurology, 34, 939–944.

* cited by examiner

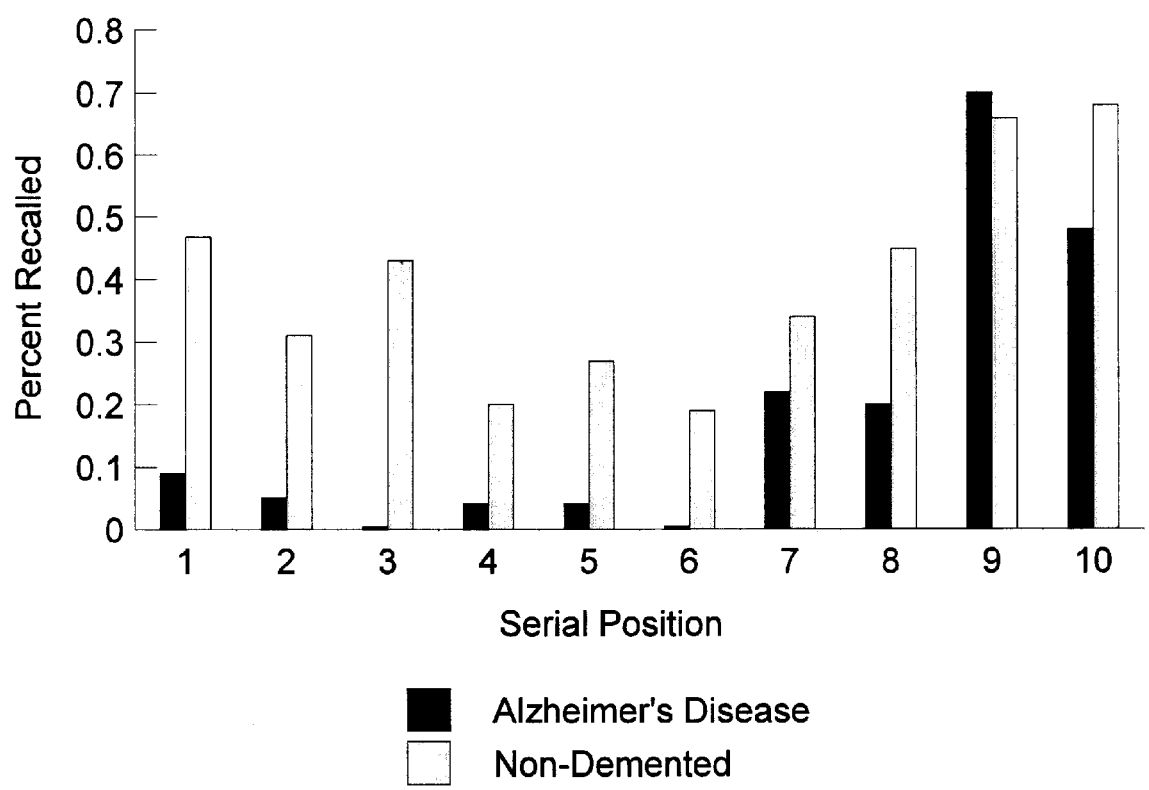

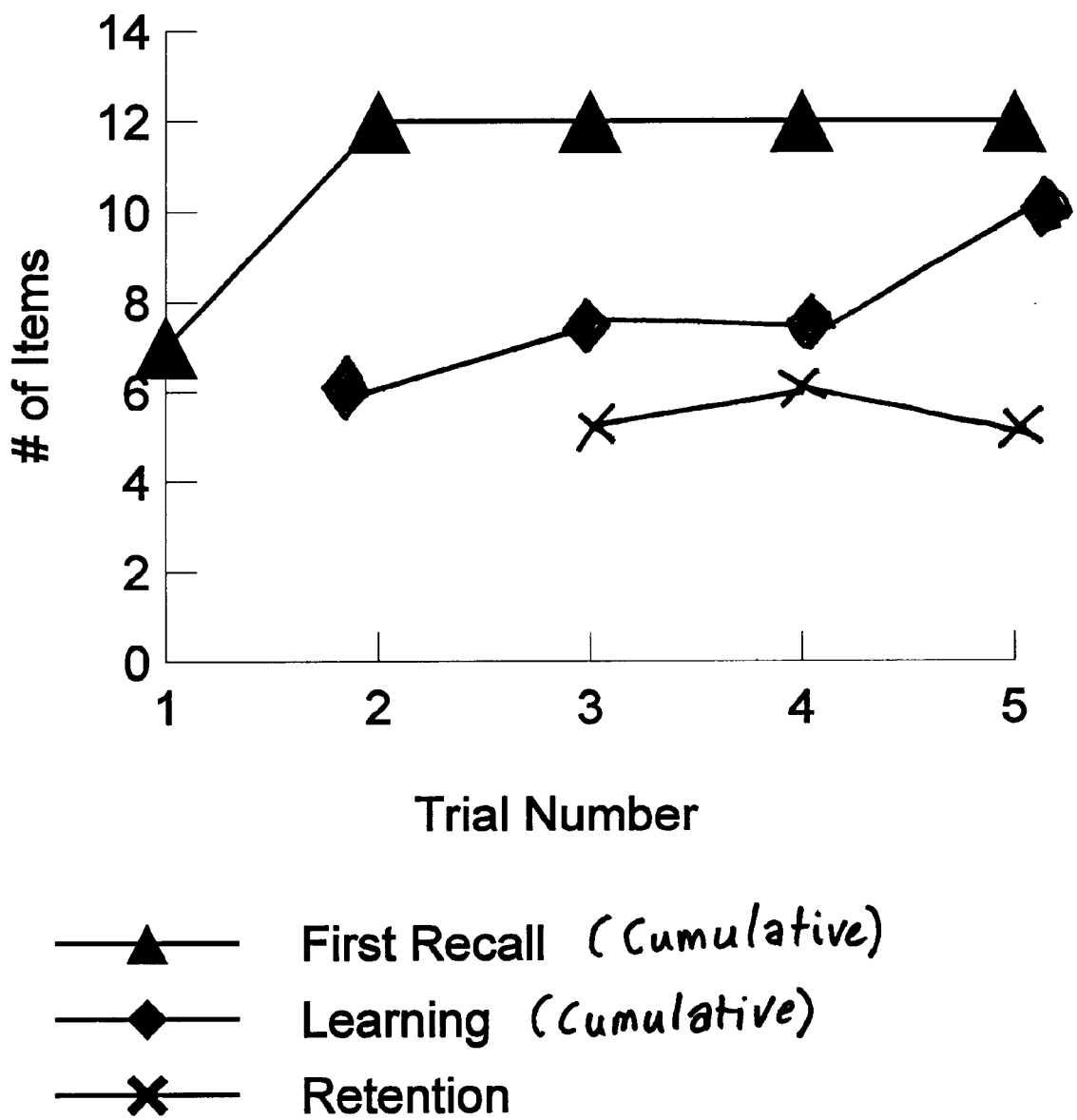

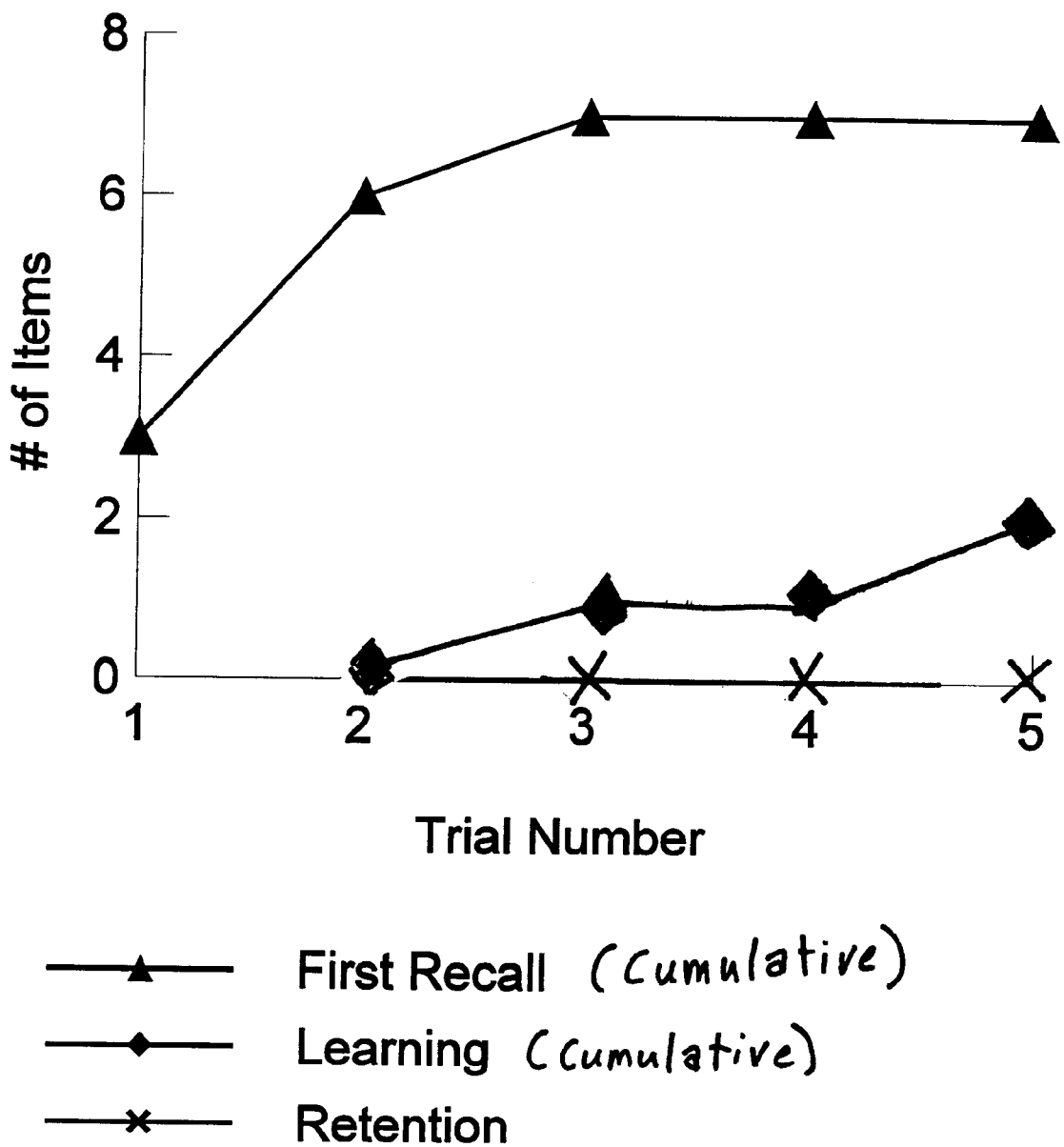

MEMORY TESTS USING ITEM-SPECIFIC WEIGHTED MEMORY MEASUREMENTS AND USES THEREOF

STATEMENT OF GOVERNMENT INTEREST

This invention was made with government support under NIH Grant No. AGO3949. As such, the United States government has certain rights in this invention.

FIELD OF THE INVENTION

This invention relates to a method for increasing the usefulness, sensitivity and specificity of tests that measure memory and facets of memory, including learning, retention, recall and/or recognition. Specifically, the sensitivity and specificity of such tests are enhanced by selectively weighting the value of specific items recalled by the test subject, either by weighting such items within any specific testing trial or across numerous testing trials. Also disclosed are various methods of reducing ceiling effects in memory tests. The invention also provides improved tests which employ item-specific weighting for the diagnosis of Alzheimer's Disease and other dementia characterized by memory impairment, as well as a method of screening for and evaluating the efficacy of potential therapeutics directed to the treatment of such dementia.

BACKGROUND OF THE INVENTION

It is estimated that over the next 20 years, one in every five persons will be over the age of 65. With this new demographic profile will come an increase in a wide variety of age-related conditions, including Alzheimer's disease ("AD") and other forms of dementia. Dementia is a syndrome of progressive decline in multiple domains of cognitive function, eventually leading to an inability to maintain normal social and/or occupational performance. At present, AD is the most common form of dementia, afflicting approximately 4 million Americans. One in ten persons over the age of 65 and nearly half of those over the age of 85 suffer from AD, and AD is the fourth leading cause of death in the U.S. The cost to U.S. society is estimated to be at least $100 billion every year, making AD the third most costly disorder of aging.

Early identification is critical in progressive conditions such as AD, because early treatment may be more effective than later treatment in preserving cognitive function. Furthermore, early detection may allow time to explore options for treatment and care. However, early detection is compromised by the failure of many patients to report early symptoms of AD to their treating physicians, including memory lapses and mild but progressive deterioration of specific cognitive functions, such as language (aphasia), motor skills (apraxia) and perception (agnosia). In addition, studies have documented the difficulty experienced by even well-trained health care professionals in correctly diagnosing AD and other forms of dementia (Callahan, et al., Ann. Intern. Med. 122:422–429, 1995). Accordingly, a simple, sensitive, reliable, and easily administered AD diagnostic test would be of great assistance in targeting individuals for early intervention.

The earliest manifestation of AD is often memory impairment, which is a requirement in each of the two sets of criteria for diagnosis of dementia that are commonly used—the National Institute of Neurological and Communicative Disorders and Stroke/Alzheimer's Disease and Related Disorders Association (NINCDS/ADRDA) criteria, which are specific for Alzheimer's disease, and the American Psychiatric Association's Diagnostic and Statistical Manual of Mental Disorders, Fourth Edition (DSM-IV) criteria, which are applicable for all forms of dementia. Therefore any test for AD or dementia associated with memory impairment should be most sensitive for the early detection of memory impairment. Conventional memory tests are not optimal for the detection of mild dementia or the early stages of Alzheimer's Disease. Some of these tests are inappropriately sensitive to the patients educational level (White and Davis, J. Gen. Intern. Med., 5:438–445, 1990; McDowell and Kristjansson, Mental Status Testing, in Measuring Health: a guide to rating scales and questionnaires, 1996:287–334). They may also fail to test for certain types of memory loss that are typical of early dementia or Alzheimer's Disease, as well as fail to reflect whether compounds or therapy administered to treat dementia are having the desired effect. These tests also often suffer from a high rate of false negatives (low sensitivity) or false positives (low specificity).

Although there are many variations, a typical memory test is structured as follows. First, the tester presents to the subject a number of items (i.e., bowl, zebra, orange, anger, etc. . . . ) to be recalled from memory. The items may be presented orally, in writing, in pictures, or by any other suitable means. Sometimes the subject is also supplied with a cue associated with each or some of the items on the list. The cue typically is the category that encompasses the associated item or defines an aspect of the associated item, i.e., the cue "animal" or "stripes" might be presented in association with the item "zebra". Certain conventional paired associate tests use unrelated nouns as cues for test items.

The presentation of items in association with a cue, where the subject must first identify the item from the cue, is known as "controlled learning". Controlled learning is used in memory tests to assure the attention of the subject and the equal processing of all the items in a list. In addition, it shows that the subjects can identify items from their cues, and induces encoding specificity, by providing cues at the time of encoding information that can later be used to aid recall. The identification of items by matching the items with the associated cues verifies that the required processing was performed by the subject.

In the next step, the subject is asked to recall the items presented to him in the list, either from memory without presentation of the associated cue, known as "free recall", or after being presented with the associated cue, known as "cued recall." Cued recall may be used selectively to facilitate recall of those items not first recalled by free recall (without any cues).

Variations of memory tests include "controlled rehearsal", which refers to a step wherein the subject is instructed to repeat each item as it is presented. Alternately, the subject may be asked to repeat the preceding item as the current item is presented, or the subject may be instructed to repeat both the preceding item and the current item. As with controlled learning, controlled rehearsal assures attention and equal processing of all items, and shows that the required processing was performed.

Some memory tests, particularly tests of delayed recall or forgetfulness, utilize interference delays between memory trials. Interference delays are periods of time between memory trials wherein an unrelated task is performed by the subject to prevent rehearsal by the subject. Common tasks performed to prevent rehearsal include having the subject count, spell, or perform a simple unrelated task.

"Controlled reminding" refers to a step wherein the subject is reminded of items that were not recalled during each trial. In free recall memory tests, the reminding would not occur until after the subject is given the opportunity to recall as many items as possible. In the case of cued recall, the subject is reminded of the item before the next cue is presented. Controlled reminding may be either "selective reminding", wherein the subject is reminded each time the item is not recalled, or "restricted reminding", wherein the subject is reminded only until the item is recalled once, either with or without presentation of the item. "Contingent learning" refers to maintaining a constant number of items to be learned. This can be done by adding new items as the old items are learned.

Memory tests known in the art include various combinations of the foregoing elements. For example, the memory component of the Free and Cued Selective Recall Test ("FCRST") is comprised of an initial controlled learning step, where the patient must first identify items from their associated cues. The patient must then recall sixteen tests items from their associated category cues. Following a brief interference delay, the patient is then asked to recall as many of the presented items as she can by free recall, i.e., without the associated cues, followed by cued recall for items not remembered by free recall. If there are multiple trials, then the subject is selectively reminded (i.e., reminded each time an item is not recalled) of missed items before the next recall trial. The score is the total of uncued responses and cued responses, with each response (whether cued or uncued) worth one point.

Conventional memory tests are scored by tallying the total number of items recalled from a list of items previously presented to the subject, either within any one testing trial or across many testing trials. Each item recalled is accorded the same weight ("unit counting" or "unweighted counting"), so that a subject recalling items 1 to 5 of a ten item list would be judged to have the same measure of memory as a subject who recalled items 6 to 10 of the same ten item list. Further, a subject recalling items 1 to 5 of a ten item list in a first trial and items 6 to 10 in a second trial would be considered to have the same measure of memory as a subject who recalled items 1 to 5 in the first and second trials, but could not recall items 6 to 10 at all. Memory tests utilizing this type of unweighted counting assume that all the items presented and retrieved are equal in value, i.e., that the probability of encoding, learning, and retaining any single item is equal to the probability of encoding, learning and retaining any other items.

However, items in such a list differ in likelihood of recall, depending on a number of factors. Serial processing at input and output almost always result in "serial position effects", which are differences in the frequency of recall among list items due to the order in which the items are presented. Simply put, some items are "harder" or "easier" to recall depending upon the order such items are presented to the subject. These serial position effects are illustrated for groups in serial position curves, which are graphs that show the percentage of subjects recalling the items of a list versus the order in which the items are presented or recalled. These serial position effects show that the probability of recall is affected by the order in which the items are presented ("presentation order"), or the order in which the items are recalled ("recall order"), or both. Important serial position effects include primacy (higher recall of earlier presented items) and recency (higher recall of the most recently presented items). Analysis of serial position effects is important because the display of certain serial position effects (or the lack thereof) may be associated with dementia. For instance, recall by normal aged subjects is characterized by primacy effects as well as recency effects, but recall by aged subjects with AD is characterized only by recency effects.

Also, unweighted counting ignores qualitative differences in memory impairment, that is, whether impairment in total memory is a result of deficiencies in a particular stage or facet of the memory process, namely a deficiency in encoding information, learning information or retaining information. Such qualitative differences may be essential for the diagnosis of AD or dementia characterized by memory impairment and to appropriately target and evaluate the efficacy of therapeutics directed to the treatment of AD or early dementia.

As a result, measuring memory by unweighted counting (i.e., unit weighting) may not be justified. Although unweighted or unit counting provides a lower bound for memory performance, it sacrifices statistical power by ignoring essential information about the serial position characteristics (probability of retrieval) of retrieved items and about the various processes involved in memory (i.e., encoding, learning and retention). A method of measuring memory that preserves information about the serial position effects of retrieved items or that pinpoints deficiencies in certain elements of total memory would improve the assessment of memory performance, aid in the earlier diagnosis of dementia and AD, and permit sophisticated screening of therapeutics directed to the treatment of AD or dementia.

SUMMARY OF THE INVENTION

Essentially all tests of memory, including tests of learning, retention, recall and/or recognition (hereinafter, "memory tests") involve "serial processing memory". Serial processing memory refers to the fact that our input and output processing is limited, so that a subject can process only one item at a time during input (i.e., receiving information) and output (i.e., recalling or retrieving information). In this sense, "memory" comprises units of received information and recalled information. In most tests of serial processing memory, multiple items are presented serially one item at a time to a subject until all the items have been presented ("serial presentation"), and the subject reports the remembered items serially one item after another ("serial recall"). Items may be presented verbally, visually, or by any other suitable means. However, all memory tests necessarily involve serial processing memory, including but not limited to, tests of narrative recall, biographical or historical recall, or category fluency tests of semantic memory. Therefore, the design and form of memory tests and experiments are limited to serial processing memory tests and experiments that test a subject's ability to encode, retain and/or retrieve items one at a time as part of a serial collection of items. Further, the encoding, retention and/or retrieval of each item is conditioned by the serial encoding, retention and retrieval of other items that precede and follow each item in presentation and recall.

Not all items presented or retrieved by a subject are equal in value. That is, the probability of encoding, learning and retaining any single item is not necessarily equal to the probability of encoding, learning or retaining any other item, depending upon a wide variety of parameters, including presentation order, recall order, etc. Some items are "harder" to recall than others, as shown by lower retrieval weights. Furthermore, the frequency and types of items not recalled by a subject can establish memory impairment and may be indicative of AD or other dementias involving memory impairment.

The present invention is directed to various methods of measuring memory in a subject comprising the use of item-specific weighting in the administration and analysis of all types of serial processing memory tests. By recognizing that not all items are of equal value, items may be selectively weighted to amplify and/or pinpoint deficiencies in memory, i.e., deficiencies in First Recall, Learning and Retention. Accordingly, the methods of the present invention improve the assessment of memory performance and aid in the earlier diagnosis of dementia characterized by memory impairment, including but not limited to Alzheimer's Disease.

One method of the present invention comprises assigning a separate weighted value to each item in a list of items to be recalled from memory based upon the length of retention of the item by the subject before recall ("Retention Weighting"). For instance, the present invention provides for the assignment of a separate weighted value for each item in a list of items to be recalled from memory based upon the item's presentation position ("Presentation Weighting"). The items are presented to a subject, and the presentation weighted values of the items actually recalled by the subject are analyzed in order to determine memory impairment. Another method of the present invention comprises presenting to a subject a list of items to be recalled from memory, recording the items actually recalled by the subject, and then assigning a separate weighted value to each item recalled by the subject based upon the item's recall position ("Recall Weighting"). The recall weighted values of items recalled by the subject are then analyzed in order to determine memory impairment. Also provided is a method comprising presenting a list of items to a subject to be recalled from memory, recording items recalled by the subject, and then assigning a separate weighted value to each item recalled by the subject based on the total length of retention of the item by the subject before recall, i.e., retention of the item from presentation to recall ("Total Retention Weighting"). The total retention weighted values of items recalled by the subject then are analyzed in order to determine memory impairment.

The present invention further provides methods for measuring memory in a subject comprising multiple memory trials that use item-specific weighting. In one embodiment of the invention, a list of items to be recalled from memory is presented to a subject and the subject is asked to recall the items presented. Items which are recalled by the subject are recorded, and at least two more memory trials are performed. Separate weighted values are assigned to each item recalled by the subject in each trial, and the assigned weighted values are analyzed to measure the subject's memory. Although any type of weighting may be used, the value of each item recalled in each trial is preferably weighted according to whether the item had been recalled in the preceding trial or the following trial, i.e., each item is weighted according to its "Recall State". Another multi-trial memory test of the present invention comprises the steps of, in a first trial, presenting a list of items to a subject to be recalled from memory, and recording items that are recalled by the subject from memory. In a second trial, items not recalled by the subject from memory in the first trial are presented again, and all items recalled by the subject from memory are recorded. More trials may be performed, with or without Selective Reminding (reminding or repeating presentation each time an item is not recalled) or Restricted Reminding (reminding or repeating presentation each time an item is not recalled, but only until initial recall of the item). After the last trial, a separate weighted value is assigned to each item recalled by the subject in each trial, and the weighted values are analyzed in order to determine memory impairment. In a preferred embodiment of the invention, the items are weighted according to whether the item has been recalled in the preceding trial or the following trial and/or according to whether the item was recalled by the subject with or without reminding.

Another method is disclosed for measuring memory in a subject, comprising the steps of serially presenting to a subject a list of items to be recalled from memory, where the items are initially presented together with an associated cue for each item and each cue is a common adjective describing the associated item. The associated cue for each item is then serially presented to the subject so that the subject may recall from memory the associated item from presentation of the relevant cue, however, the cues are serially presented in reverse order than the initial serial presentation order. Items recalled by the subject after presentation of the associated cue are recorded and assigned a separate weighted value, wherein the value for each item is weighted according to the period of retention of the item by the subject before recall. The assigned values of items recalled by the subject can then be analyzed to determine memory impairment.

Also disclosed by the present invention are methods of reducing ceiling effects in serial processing memory tests, comprising introducing a period of extended delay between (a) presentation of a list of items to a subject wherein said items are to be recalled from memory by the subject and (b) first recall of the items by the subject from memory. Alternatively, ceiling effects may be reduced in serial processing memory tests which use free and cued recall by selectively weighting items recalled by the subject by free recall. The results may then be analyzed to establish memory impairment and to determine whether there is indication of dementia characterized by memory impairment or AD.

Further provided is a method of screening agents directed to the treatment or prevention of dementia characterized by memory impairment, including AD, said method comprising comparing a subject's or a group of subjects' performance on any of the item-specific weighted memory tests of the present invention before adminstration of the selected agent and after administration of the selected agent to the subject or group of subjects. Alternatively, the results of item-specific weighted memory tests performed by control groups not receiving the selected agent and test groups receiving the selected agent may be compared.

Additionally, the invention provides a method of screening such agents comprising administering any unweighted or unit scored serial processing memory test to members of a control group that have not received the selected agent and to members of a test group that have received the selected agent. Serial position curves using the results of the memory tests are then generated for both the control group and the test group, and the effect of the agent on memory function is determined by comparing the serial position curves of the two groups. Alternatively, the items in the generated serial position curves can themselves be weighted and the the weighted serial position curves of the two groups may be compared. Also disclosed is a method of screening such agents comprising analyzing the serial position curves derived from unweighted serial processing memory tests administered to a subject or a group of subjects before and after treatment of the subject(s) with the agent being screened. The items in the serial position curves may be weighted and the weighted serial position curves can be compared.

It is understood that, in all of the methods of the present invention, assigned values may be analyzed by calculating a score for the subject based on the weighted values of recalled items, and then comparing the score to a reference score. The reference score may establish memory impairment or be indicative of a dementia characterized by memory impairment, including, but not limited to, Alzheimer's Disease. Further, items may be weighted according to any convenient, useful or desirable parameter, including, but not limited to, retention weighting (presentation weighting, recall weighting and total retention weighting), recall state, normative weighting, amplification weighting, retrieval weighting or weighting based upon serial position effects.

Additional objects and embodiments of the invention will be apparent from the description which follows.

BRIEF DESCRIPTION OF THE FIGURES

FIG. 1 represents the serial position curves of free recall of a 10-item list by a group of non-demented aged subjects and a group of aged subjects with AD. The frequency of recall of each item by each group is shown as a function of each item's position in the list.

FIG. 2 represents the stages of recall or memory by a healthy aged individual without AD (graphically representing the data of Table 7). First Recall is represented as the cumulative number of list items recalled for the first time after presentation. 7 of 12 items were recalled for the first time on the first trial, and the remaining 5 items were recalled for the first time on the second trial. Learning is represented as the cumulative recall of items on the next trial, without presentation. 6 of the 7 items recalled for the first time on the first trial were recalled on the next trial, without presentation. 1 more item was learned in the third trial, and 3 more items were learned on the fifth trial. Retention is represented as the number of previously learned items that are recalled on that trial, without presentation. The normal aged individual retained most items learned in previous trials.

FIG. 3 represents the stages of recall or memory by an aged subject with AD. The stages are as described above for FIG. 2. Only 3 of 12 items were recalled for the first time on the first trial, and only 3 more items were recalled for the first time on the second trial. Scarcely any of these items were learned, as shown by the failure to recall them without presentation in subsequent trials. No items were retained in five trials.

DETAILED DESCRIPTION OF THE INVENTION

The present invention is directed to a method of measuring the memory of a subject which employs item-specific weighting of items presented to and/or recalled by a test subject in serial processing memory tests. While the preferred embodiment of the present invention comprises the use of item-specific weighting in serial presentation/serial recall memory tests, the item-specific weighting of the present invention may be used in conjunction with any form of serial processing memory test, including but not limited to, actions, events, tests of visual input, narrative testing, tests of biographical or historical memory, or category fluency tests of semantic memory. Items may be weighted within a memory trial, or across two or more memory trials.

As used herein, "weighting" refers to the assignment of a numerical value to each item of a serial processing memory test to be recalled by the subject, where the values assigned to each item are determined according to the phenomena observed with recall of such items. For example, items may be weighted according to the difficulty of recall, so that items that are harder to recall (e.g., items that are recalled in the absence of any cues or other means to assist in recall, i.e., "free recall") will be weighted more than items that are easier to recall (e.g., items that are recalled in response to a cue previously associated with that item, i.e., "cued recall"). Items may be weighted according to the length of retention by the subject before recall ("retention weighting"), i.e., by the order of presentation to the subject ("presentation weighting"), their order of recall by the subject ("recall weighting") or by the total period between presentation of the item and recall of the item by the subject ("total retention weighting"). In addition, items in a multi-trial memory test may be weighted according to whether that particular item was recalled in the preceding and/or the subsequent trial ("recall states"), and further weighted according to any of the parameters noted above. Additionally, items may be weighted with respect to a group of normal subjects, so that items most often recalled by normal subjects are given more weight ("normative weighting"), or may be weighted to enhance the differences between two groups, so that items typically recalled by one group but not by another are given greater weight ("amplification weighting"). Finally, items may be weighted according to the frequency of recall of that item in serial position curves generated from reference groups. Conversely, items in serial position curves may be weighted according to any of the parameters noted herein (i.e., according to presentation order, for example), in order to generate "weighted" serial position curves.

Specifically, the present invention discloses a method for measuring memory in a subject, comprising presenting a list of items to be recalled from memory to a subject, where each item in the list of items is assigned a separate weighted numerical value. Items recalled by the subject from memory are recorded and the assigned values of the items recalled by the subject are analyzed. In one embodiment of the invention, a score is calculated based on the assigned numerical values and the resulting score is analyzed in relation to a reference score. The reference score may establish memory impairment or indicate a dementia characterized by memory impairment, including but not limited to Alzheimer's Disease. In one preferred embodiment of the invention, the numerical values assigned to the items of the list are weighted according to presentation order so as to amplify primacy effects, i.e. presentation weighting. By way of example, the first item presented in a ten item list may be given a value of 10, the second item a value of 9, the third item a value of 8, etc., so that the last item presented to the subject would be given the lowest value of 1. The weighted values then may be analyzed to determine whether there is a loss of primacy in the subject, or some other indicator of memory impairment. A score may be calculated based on the assigned weighted values of the items successfully recalled by the subject, and analyzed in relation to a reference score which establishes the level of memory impairment in relation to the chosen reference group or in relation to an earlier score obtained by the subject. The reference score may establish memory impairment, or indicate a dementia characterized by memory impairment, including Alzheimer's Disease.

The invention also provides a method for measuring memory in a subject, comprising presenting a list of items to be recalled from memory by the subject and recording the items so recalled as well as their order of recall, assigning a separate weighted numerical value to each item recalled (as opposed to each item presented), calculating a score based on the assigned weighted numerical values and analyzing the weighted values in order to evaluate the subject's memory. In a preferred embodiment of the invention, the numerical values assigned to the items recalled by the subject are weighted according to recall order, i.e., "recall weighting". By way of example, the first item recalled by the subject may be assigned a value of 1, the second item recalled may be assigned a value of 2, etc., so that if the subject recalled 10 items, the tenth item recalled would be assigned a value of 10. Recall weighting may be appropriate when presentation order does not apply, such as in Category Fluency Tests of semantic memory (i.e. general memory not tied to any particular learning experience). A score may be calculated based on the assigned weighted values of the items successfully recalled by the subject, and analyzed in relation to a reference score which establishes the level of memory impairment in relation to the chosen reference group or in relation to an earlier score obtained by the subject.

Also disclosed by the present invention is a method for measuring memory, said method comprising the steps of presenting a list of items to a subject to be recalled from memory by the subject and recording items actually recalled by the subject, together with their recall order. Separate weighted numerical values are assigned to each item recalled based upon the length of retention of the item by the subject before recall of that item ("total retention weighting"), and the assigned values of items recalled by the subject are analyzed in order to evaluate the subject's memory. Specifically, the items are weighted according to the total interval between presentation of the item to the subject and recall of that item by a subject, although the items may be further weighted according to other parameters as described herein. By way of example, items presented first and recalled last by the subject would be give the greatest weight, while items presented last and recalled first would be given the least weight. Alternatively, weighted values for each item may be calculated by summing the presentation order of an item with the recall order of that item. Accordingly, in a ten item list, the first three presented items would be assigned numerical values of 10, 9, and 8, respectively, so that the last item presented to the subject would be assigned a numerical value of 1. Further, the first few items recalled by the subject would be assigned numerical values of 1, 2, and 3, respectively, so that the last item recalled by the subject would be assigned the highest numerical value (e.g., a value of "7" should the subject recall seven items). The retention weighted values for each item would then be calculated by summing the presentation position and recall position for that item.

Such weighting takes into account that some items are recalled by the subject soon after presentation, while other items are recalled only after the presentation and recall of other items, with more credit being given to items that are retained in memory longer. Therefore, Total Retention Weighting provides a measure of the effectiveness of memory reflecting the relative difficulty of remembering each item. In a preferred embodiment, the weighted values are analyzed by calculating a score based on the weighted values of the recalled items and comparing the score to a reference score. As noted above, the reference score may establish memory impairment or indicate a dementia characterized by memory impairment, including Alzheimer's Disease.

Also presented is a method for measuring memory in a subject, comprising item-specific weighting in multi-trial memory tests. In a first trial, a list of items is presented to the subject to be recalled from memory, and items actually recalled by the subject are recorded. At least two more trials are performed (although as many trials as are deemed necessary by the skilled practitioner may be employed), and in each trial a separate weighted numerical value is assigned to each item recalled by the subject. Selective Reminding may also be used, where the subject is reminded (i.e., the item is presented) each time an item is not correctly recalled. Alternatively, Restricted Reminding may be used, where the subject is reminded only until the item is recalled for the first time.

Although any type of weighting that is used in the single trial memory tests described above may be used in multi-trial memory tests, in the preferred embodiment of the invention, the items are weighted according to whether the item has been recalled in the preceding trial or in the following trial. In one embodiment, items not recalled in the previous or following trials are given the lowest weight, while items recalled both on the preceding trial and the following trial are given the highest weight. Other embodiments further weight items according to whether they were recalled with or without presentation or reminding in each trial. The weighted values may be analyzed by calculating a score based on the weighted values of the recalled items and comparing the score to a reference score. The reference score may establish memory impairment or indicate a dementia characterized by memory impairment, including Alzheimer's Disease.

In a more preferred embodiment, recalled items in each trial are assigned "Recall States" which represent the status of itemized recall across trials. Recall States are sufficient to identify and describe the four possible scenarios in recalling a specific item across trials. The four possible Recall States are summarized below in Table 1:

TABLE 1

| Recall State Number | Recall State | Criteria |
| --- | --- | --- |
| 1 | 0-1-0 | Not recalled on preceding trial<br>Not recalled on next trial |
| 2 | 0-1-1 | Not recalled on preceding trial<br>Recalled on next trial |
| 3 | 1-1-0 | Recalled on preceding trial<br>Not recalled on next trial |
| 4 | 1-1-1 | Recalled on preceding trial<br>Recalled on next trial |

Accordingly, for each trial wherein an item is recalled, the Recall States reflect whether the same item was recalled on a previous trial and whether the same item was recalled on a subsequent trial. A -0- indicates failure to recall an item, while a -1- indicates recall of that item. Thus, Recall State 1 shows that the recalled item was not recalled on either the preceding trial, nor was it recalled on the subsequent trial. Recall State 4 shows that the recalled item was on both the preceding trial and on the subsequent trial. It is understood that the Recall State cannot be measured on the last trial, since there is no subsequent trial from which to determine the appropriate Recall State. Recall of an item in the first trial is assigned a Recall State of "1" or "2" (depending on whether that item is recalled in the next trial), despite the technical absence of a previous trial.

Recall States correspond to the stages or component parts of memory. Specifically, the stages of memory include First Recall, Learning and Retention. "First Recall" is when an item is recalled for the first time in a multi-trial memory test, with or without presentation or reminding. "Learning" is shown when an item is recalled on the next trial after initial or First Recall, with or without presentation or reminding. Finally, "Retention" is shown where an item is recalled across two successive trials after First Recall (i.e., across at least three successive trials in total), with or without presentation or reminding.

Analysis of weighted Recall States using the method of the present invention can yield valuable information regarding deficiencies in the various components of a subject's memory, and can be used to diagnose memory impairment, or indicate a dementia characterized by memory impairment, including AD. The number of trials needed by a subject to reach First Recall, then Learning, and then Retention of an item will illustrate deficiencies in each particular stage of memory and may be indicative of dementia or AD. For instance, subjects with AD take longer to reach First Recall of items and may not be able to learn items after First Recall.

The analysis of multi-trial memory tests using Recall States may comprise calculating a score for the subject based upon the weighted Recall States and comparing the score to a reference score which may establish memory impairment or indicate dementia characterized by memory impairment. Preferred methods of scoring multi-trial memory tests using Recall States include conventional unit scoring (the number of items recalled), itemized recall scoring (the number of times each Recall State was achieved for each item) and most preferably, aggregate scoring of all Recall States in each trial, hereinafter termed the "Itemized Score" or the "Iscore". It is understood that since Recall States correspond to the various stages of memory (i.e., First Recall, Learning and Retention), depending upon what facet of memory is being investigated, the various Recall States may be further weighted to amplify phenomena associated with deficiencies in First Recall, Learning or Retention. Therefore, the Iscores may be a weighted score depending upon the relative values assigned to the four Recall States, and the resulting weighted score may be used to amplify deficiencies in specific elements of memory. Further, where Selective Reminding is used (i.e., where the subject is reminded in each trial of items not recalled in the previous trial), the sum of Recall States 3 and 4 may be calculated to provide a measure of non-presentation recall (hereinafter "Non-Presentation Recall"), indicating the total number of occurrences of recall without presentation of the item, within each trial or across trials.

Further disclosed is a method for measuring memory in a subject, said method comprising serially presenting to a subject a list of items to be recalled from memory, together with an associated cue for each item. In a preferred embodiment of the invention, the associated cue is an adjective describing the item to be recalled, e.g., "dirty" may be a cue for "sock", or "big" may be a cue for "fish". Following presentation of the items and their associated cues, the cues are serially presented to the subject and the subject is then asked to recall the item associated with the given cue. In a preferred embodiment, the associated cues are presented in the reverse serial order from the initial presentation order. Each item successfully recalled by the subject from the associated cue is then total retention weighted, i.e., is weighted according to the length between the presentation order and recall order of the item. It can be seen that increased periods of retention may be obtained by presenting the associated cues in reverse order than the initial presentation order, since items presented first will be recalled last by the subject. The increased range of retention times provides a broader range of difficulty in recalling certain items, and widens test results between those suffering from memory impairment or AD from normal non-demented individuals. Weighted values may be analyzed in order to determine memory impairment, including calculating a score for the subject based on the weighted values and comparing the score with a reference score to establish memory impairment or dementia.

Any of the methods of the present invention herein above may be used to yield indicators of dementia characterized by memory impairment or AD. However, it can be appreciated by the skilled practitioner that it would be more economical and time saving to initially perform a highly sensitive memory test that screens for AD before performing the more extensive methods of the present invention. In particular, the subject or a group of subjects initially may be screened with the Memory Impairment Screen (Buschke, et al., Screening for dementia with the Memory Impairment Screen, Neurology 1999; 52:231–238) in order to exclude non-demented individuals from more extensive testing and increase the specificity of these more extensive tests. Accordingly, the present invention discloses a two-stage method of measuring memory in a subject, comprising the first stage of administering the Memory Impairment Screen in order to exclude individuals with no memory impairment, and then a second stage of diagnosing memory impairment or dementia using any of the methods disclosed herein.

Specifically, in the screening step, the subject is presented with four items to be recalled from memory. In an optional controlled learning step, the subject is asked to read the items aloud and then to identify and name each item in association with a presented cue (e.g., the subject identifies "potato" when the tester states the cue "vegetable"). After an interference delay and prior to initial recall, the subject is asked for the free recall of the four items in any order. The associated cues are presented to elicit recall of those items not retrieved by free recall. Then the number of items retrieved by free recall and the number of items retrieved by cued recall are recorded. The MIS score is calculated by selectively weighting free recall, for example, by scoring the test as (2×free recall)+cued recall. Subjects receiving scores suggesting memory impairment or dementia are then given a second stage sixteen item FCRST, although items in the FCRST are weighted according to the method of the present invention by selectively weighting items recalled without presentation (i.e., items recalled by free recall). Such weighting may be termed as "retrieval weighting". Other methods of weighting as disclosed herein may be used in addition to the retrieval weighting.

Various methods for reducing ceiling effects in serial processing memory tests are also disclosed. "Ceiling effects" occur when a significant proportion of test subjects perform so well in a memory test that distinction among the subjects is hindered. Accordingly, ceiling effects reduce the sensitivity of a diagnostic test because they increase the number of false negatives, i.e., too few people are diagnosed with memory impairment. The present invention provides that the introduction of an extended delay (preferably an interference delay) after initial presentation of items and before the subject's first attempt at recall of those items greatly reduce recall and prevents ceiling effects in both unweighted conventional memory tests and the weighted memory tests of the present invention. Without being bound to theory, the inventor theorizes that the introduction of a period of extended interference delay before recall increases the difficulty of recall, and thereby better distinguishes between subjects having mild memory impairment or pre-clinical AD and normal individuals.

The period of delay may range from 30 seconds to 30 minutes, and is preferably 5 minutes, more preferably 10 minutes, and most preferably at least 15 minutes. The delay comprises any exercise that prevents rehearsal, including but not limited to simple number exercises (copying of even digits, adding 1 to odd digits, adding one to a number and copying the sum, etc.) or simple word exercises (reporting words which are spelled backwards to the subject, reporting words that are spelled forwards, or a combination of reporting backwards and forward spelled words, etc.). The use of interference delays before initial recall to reduce ceiling effects is novel and is considered part of the present invention in combination with any standard memory tests where ceiling effects are exhibited. All other uses of interference delays that are known by the inventor are used following or between memory trials to test delayed recall or forgetfulness, and do not result in the reduction of ceiling effect as noted herein.

Ceiling effects in memory tests which use free recall (recall of items by the subject without presentation of associated cues) and cued recall (recall of items in response to presentation of associated cues) (such as the 16 item FCRST) may also be reduced by selectively weighting items which are recalled without the presentation of cues (i.e., by free recall).

Finally, the present invention discloses various methods to screen agents directed to the treatment or prevention of dementia characterized by memory impairment, including AD. One method comprises performing one or more of the memory tests of the present invention using item-specific weighting in order to obtain a reference score for a test subject. Then, the agent being screened is provided to the subject and the memory tests are repeated. The effect of the selected agent can be evaluated by comparing the scores of the memory tests administered before and after treatment with the agent being screened. Alternatively, one or more of the memory tests of the present invention using item-specific weighting may be administered both to a control group not receiving the agent being screened, and to a test group receiving the agent being screened. The effect of the selected agent on the test group is evaluated by comparing the scores of the control group and the test group. Another method to screen agents directed to the treatment or prevention of dementia characterized by memory impairment involves analyzing the serial position curves generated from administering conventional memory tests, either by comparing the curves generated by test groups receiving the selected agent with control groups, or by comparing the curves generated by one group before and after administration of the agent being screened. Alternatively, the serial position curves generated from these groups may be selectively weighted, so that items in the serial position curves are weighted according to presentation order, or any other suitable parameter.

It is understood that the present invention includes any and all of the above noted methods used to measure memory in a subject and any variations thereof that may be apparent to the skilled practitioner, and includes all serial processing memory tests using weighted memory measurements to diagnose or screen for memory impairment, indicate dementia (including AD or early AD), or deficiencies in any stage of recall, learning or retention. It is understood that such memory tests may include elements or combinations of elements such as free recall, cued recall (including forward cued recall or reverse cued recall), controlled learning, controlled rehearsal, controlled reminding (including selective reminding or restricted reminding), and/or contingent learning, as appropriate.

The present invention is described in the following Experimental Details Section which is set forth to aid in the understanding of the invention, and should not be construed to limit in any way the invention as defined in the claims which follow thereafter.

Experimental Details

I. Weighting Within a Single Trial

A. Item-Specific Weighting Based on Presentation Order

To examine the effects of differential weighting and to determine if memory measurement and discrimination of memory impairment might be improved by appropriate weighting of recall, the assessment of memory by unweighted recall ("free recall") and by retention-weighted recall (or retention weighting, hereinafter "RWR") were performed within a single trial of normal aged subjects and subjects with AD. Free recall was compared to RWR in 228 normal aged subjects and 24 subjects with AD, using a 10-item list. The community-dwelling sample was recruited for the longitudinal Einstein Aging Study by systematic telephone screening from the local Health Care Finance Administration (HCFA) list, which includes most adults aged 65 years and over. These subjects received extensive neuropsychological testing, and neurological examination and other diagnostic tests when indicated. AD was diagnosed by the NINDS/ADRA criteria. The two groups were similar in age, years of education and gender balance. As expected, the AD group had a lower mean WAIS Verbal IQ test score and made more errors on the BIMC mental status test.

The subjects were given a 10-item free recall test based on the Telephone Interview for Cognitive Status. The 10 items were recited to the subjects, and the subjects were then asked to repeat as many words as they could remember, in any order. Free recall was measured by a traditional unweighted counting of the number of items recalled, and RWR was measured by a simple version of retention-based weighting the items recalled. Examination of serial-position curves showed that recall by normal aged subjects was characterized by primacy effects as well as recency effects, but recall by aged subjects with AD was characterized only by recency effects (FIG. 1, Table 2).

TABLE 2

|  | Normal Aged | Aged with AD |
|---|---|---|
| Recency (last three items) | 60% | 46% |
| Primacy (first three items) | 39% | 4% |
| Difference (Recency - Primacy) | 21% | 42% |

In contrast to normal aged subjects, aged subjects with AD remember recent items far more frequently than early items. Therefore, differences in recall by normal aged subjects relative to aged subjects with AD can be differentially amplified by weighting that gives more value to recall of early items than to recall of recent items. As a result, the discriminatory power of the measurement is enhanced. A simple form of RWR, i.e., weighting by presentation order, was employed by scoring 10 for recall of the first item presented, 9 for recall of the second item presented, etc. down to 1 for recall of the last presented item. Table 3 compares the means and standard deviations (S.D.) of Free Recall and RWR for a non-demented aged subjects and aged subjects with AD. Comparison of unweighted free recall and RWR by aged with and without AD showed that RWR increased the effect size (Table 3). Effect size estimates the magnitude of the difference in standard deviations between mean recall by normal aged and aged with AD, and is calculated by dividing the difference in mean recall by the pooled standard deviation. RWR scoring doubled the effect size relative to free recall.

TABLE 3

| Memory Measure | Normal Aged (mean (S.D.)) | Aged with AD (mean (S.D.)) | Effect Size |
|---|---|---|---|
| RWR | 5.0 (5.3) | 18.9(11.4) | 1.26 |
| Unweighted Free Recall | 1.8 (1.3) | 3.9(1.7) | 0.64 |

In addition, RWR improved discrimination of AD by increasing specificity without decreasing sensitivity. Discrimination is shown by sensitivity and specificity relative to an accepted gold standard of diagnosis. In this case, the gold standard employed was the NINDS/ADRDA diagnostic criteria for AD. Sensitivity measures the proportion of those with dementia who are correctly identified as demented. Specificity measures the proportion of those without dementia who are correctly defined as non-demented. Accordingly, the more sensitive a test is, the more likely that normal subjects will be incorrectly diagnosed with AD (i.e., there will be more false positives). The more specific a test is, the more likely that subjects with AD will not be detected (i.e., there will be more false negatives).

Table 4 compares the specificity of free recall and RWR at a common sensitivity value of 92%, as derived from graphs of sensitivity vs. specificity for free recall and RWR. When the sensitivity is 92%, the specificity of free recall is 57%, but the specificity of RWR is 74%. The 17% higher specificity of RWR means that RWR correctly classified 40 non-demented aged who were misclassified as demented aged when tested by free recall.

TABLE 4

| Memory Measure | Sensitivity | Specificity |
|---|---|---|
| RWR | 92% | 74% |
| Unweighted Free Recall | 92% | 57% |

RWR has greater discriminatory power than free recall, because RWR has a higher specificity at the same level of sensitivity. This example suggests that memory measurement and discrimination of memory impairment might be improved by appropriate weighting of recall.

B. Item-Specific Weighting Based on Recall Order

Retention-based weighting is influenced by what happens to each item in the interval between presentation (encoding) and retrieval (testing). What happens between presentation and retrieval of each recalled item can be evaluated in terms of (1) the number of items presented (and encoded) after each item was presented (presentation order or position), and (2) the number of items retrieved before each item was retrieved (recall order or position). In the simple retention-weighted recall memory measure described above, each item was weighted according to its relative length of retention before recall began (i.e., presentation order). A more comprehensive measure of retention-weighted recall can be obtained by weighting not only with respect to the position of items presented before recall begins, but also with respect to the order in which those items are recalled. Such a measure requires information about the serial recall order of recalled items as well as their serial presentation order. Such a retention-weighted memory measurement can be broken down into a "presentation component", weighted in terms of the number of items presented after each item, and a "recall component", weighted in terms of the number of items recalled before each item recalled.

The complete Presentation-Recall Interval or Retention Period consists of the number of items presented after each item (presentation component) plus the number of items recalled before each item (recall component). These two components result in three possible weighting protocols. First, there may be Total Retention Weighting. Second, there may be Presentation weighting alone, and last, there may be Recall weighting alone. For each item recalled, weighted scores are calculated according to one of the algorithms below and then the weighted scores are summed to obtain the weighted score of each trial.

(a) Total Retention Weighting:=(List Length−Presentation Position)+Recall Position (b) Presentation Weighting:=(List Length−Presentation Position)+1

(c) Recall Weighting:=Recall Position

For example, suppose items A, B, C, and D are presented in that order. Item A is assigned a value of 4, item B a value of 3, item C a value of 2, and item D a value of 1. In this case, serial presentation of items A, B, C, and D, followed by serial recall of D, C, and A (but not B) yields the following Presentation-Recall Weighting scores for each item: Item D:

(4−4)+(1)=1

Item C: (4−3)+(2)=3

Item A: (4−1)+(3)=6

The total Retention Weighted score for this trial is obtained by adding the weighted scores of all recalled items. In the above case, the total retention-weighted recall score would be 10. Instead of counting only the number of items retrieved, which ignores the fact that some items are retrieved soon after presentation while other items are retrieved only after presentation and retrieval of other items, such Retention Weighted scoring provides a measure of the effectiveness of memory that takes into account the relative difficulty of remembering each item (i.e., the relative retention of each item) by giving more credit for recall of items that were retained longer.

Presentation weighting alone may be appropriate when information about recall order is not available, when recall order is random, or when recall order may obscure the effects of presentation ordering. Recall weighting alone may be appropriate when presentation does not apply, as in Category Fluency tests of semantic memory. Retention Weighting may be appropriate for tests involving reverse cued recall, where the order of recall is controlled.

The benefit of Retention Weighting can be maximized through use of Reverse Cued Recall, as illustrated in Table 4A below. As can be seen from the Table, unweighted unit counting cannot distinguish between two healthy aged subjects, who both recalled six items on the 12 item memory test. However, when reverse cued recall is used and retention weighted, the healthy aged male obtains a retention weighted score of 40, revealing a better memory performance than the healthy aged female, who receives a retention weighted score of 31. Reverse Cued Recall maximizes the range of retention (and therefore difficulty) tested. Since the first item presented is the last item tested, it provides the lengthiest retention period. Conversely, the last item presented is the first item tested, and provides the shortest retention period.

Also worth noting is the use of Coherent Paired Associates. Conventional Paired Associate tests use "unrelated" nouns as cues and targets, which requires the subject to generate a mediator to relate the cue and the target nouns.

The requirement to generate mediators can confound memory test results, especially for those subjects that have difficulty generating the appropriate mediator, even in the absence of traditional memory impairment. Coherent paired associates, as shown in Table 4A, use common adjectives as associated cues to elicit recall of their associated noun targets. These cues can be related to their targets without additional mediators, so that memory performance does not depend on the generation of mediators.

TABLE 4A

Coherent Paired-Associates (CPA): Reverse Cued Recall

| Associated Cue | Target | test order | Healthy Aged (BIMC = 2) 78 M, ed = 13 | Healthy Aged (BIMC = 2) 81 F, ed = 12 |
|---|---|---|---|---|
| Small | City | 12 | X | X |
| Hard | Mattress | 11 | 11 | X |
| Expensive | Shoes | 10 | 10 | 10 |
| Boring | Movie | 9 | 9 | X |
| Suprising | Story | 8 | X | X |
| Torn | Pajamas | 7 | X | 7 |
| Hungry | Snake | 6 | X | 6 |
| Huge | Fish | 5 | 5 | X |
| Greasy | Knife | 4 | 4 | 4 |
| Noisy | Restaurant | 3 | X | 3 |
| Special | Watch | 2 | X | X |
| Empty | Cup | 1 | 1 | 1 |
| Cued Recall | | | 6 | 6 |
| Cued Recall/12 | | | 0.50 | 0.50 |
| Retention Weighted Score | | | 40 | 31 |
| Retention Weighted Score/78 | | | 0.51 | 0.40 |

II. Item-Specific Weighting Across Trials

A. Significance of Recall States

In addition to the single-trial recall protocols described above, memory testing often relies on multi-trial recall tests to further evaluate learning. As in the case of single-trial recall protocols, individual multi-trial recall protocols exhibit great variability in the pattern of recall of individual items across trials. Some items are recalled on all trials from the very first trial, some are never recalled at all, others are recalled on some trials but not on others, and so on. Such variability in recall across trials can be classified into a limited number of recall states, according to empirical criteria concerning recall on the preceding trial and the following trial, as well as the current trial. These recall states provide information about the stages of learning that may assist measurement of memory function.

B. Recall States

Learning of items across trials involves three states of recall: First Recall of each item; Learning, shown by further recall of that item after initial recall; and Retention, shown by further recall of that item after Learning. Learning may be impaired at any of these recall stages. Learning cannot begin without an initial recall, learning cannot occur if the initial recall does not result in further recall, and learning cannot proceed to Retention if recall from the Learning step does not result in recall on the next trial. While any of these three stages may be affected in the memory impairment associated with Alzheimer's disease, impairment of learning at the second stage (Learning) that results in failure of further recall may be critical for detecting memory impairment in early Alzheimer's disease.

FIG. 2 shows the stages of recall by a healthy aged individual without Alzheimer's disease. In this healthy aged individual, First Recall of many items occurred early. However, and in particular by Trial 2, many of those items were not encoded for recall from long term storage, since only about half of the items were recalled without presentation on the next trial. Most of the items recalled without presentation were recalled again on the next trial.

FIG. 3 shows the stages of recall by an aged person with AD. In this aged AD individual, the First Recall of the items occurred much later, and some items were never recalled at all. Hardly any of the items initially recalled were thereafter recalled without presentation. Because very few items were recalled without presentation, continuing recall on the next trial could not be assessed.

Analysis of how these stages are affected and the relative severity of their impairment can provide the basis for more sensitive and more specific tests of AD memory impairment. These tests may be designed to detect changes in specific components of recall that may be affected earlier or more severely in AD. The tests may be performed with selective reminding, with restrictive reminding, or with reminding of all items in all trials. In the following examples of recall across trials it is apparent that there is considerable variation in the recall of different items across trials (rows). More accurate assessment of recall across trials can be achieved by weighting that takes into account the recall state(s) of each item on successive trials, i.e., its effect on recall on the next trial. In these first two examples of recall across trials by selective reminding (i.e., the subject is reminded each time the item is not recalled), the numbers in each trial (T1 through T6 in Tables 5 and 6) indicate the order in which those items were recalled on that trial. Numbers in shaded cells show recall of that item on that trial without presentation (i.e., reminding) of that item on that trial. Numbers in clear cells indicate recall of that item on that trial with presentation (i.e. reminding) of that item on that trial. The number in the far right cell of each row is the number of trials on which that item was recalled. The consistency with which items are recalled across trials varies, even when total recall across trials is the same.

TABLE 5

Healthy Aged Individual

| Item | T1 | T2 | T3 | T4 | T5 | T6 | total # of trials items recalled |
|---|---|---|---|---|---|---|---|
| Bowl | 6 | 3 | 5 | 6 | 7 | 9 | 6 |
| Passion | | 3 | | 4 | 2 | 4 | 4 |
| Dawn | | 10 | | 10 | | 3 | 3 |
| Judgement | 4 | 7 | 6 | 8 | 6 | 10 | 6 |
| Grant | | 4 | 6 | 6 | 8 | 11 | 5 |
| Bee | 3 | 11 | 7 | 7 | 4 | 6 | 6 |
| Plane | | 2 | | 2 | | 1 | 3 |
| County | | 1 | | 11 | 5 | 7 | 4 |
| Choice | 7 | 8 | 3 | 6 | | 2 | 5 |
| Seed | 5 | 6 | 4 | 5 | 9 | 5 | 6 |
| Wool | 2 | | 1 | | 1 | 8 | 4 |
| Meal | 1 | 5 | | 1 | | 3 | 4 |

Consistency of recall shows the effect that recall of an item on one trial has on recall of that item on the next trial. The effect that recall of an item has on its recall on the next trial provides the basis for describing, measuring, analyzing, and accounting for increasing recall across trials. In the example in Table 5 (above) of good learning across trials by a healthy aged person without AD, recall of an item on one trial most frequently resulted in recall without presentation (shaded cells) of that item on the next trial. Once an item was recalled without presentation, it was almost always recalled again on the next trial without presentation.

The following example of impaired learning across trials by an aged individual with AD and vascular dementia also shows variable recall across trials (Table 6). Both the total number of trials on which an item was recalled and the consistency of recall (i.e., the effect of recall of an item on recall of that item on the next trial) varied among items.

TABLE 6

Aged Individual with AD and Vascular Dementia

| Item | T1 | T2 | T3 | T4 | T5 | T6 | total # of trials items recalled |
|------|----|----|----|----|----|----|----|
| Shine    |   |   |   |   |   |   | 0 |
| Disagree |   |   |   |   |   |   | 0 |
| Fat      |   |   |   |   |   |   | 0 |
| Wealthy  |   |   |   |   | 4 |   | 1 |
| Drunk    |   |   |   |   |   |   | 0 |
| Pin      |   | 2 |   | 3 |   | 3 | 3 |
| Glass    | 3 |   |   |   |   |   | 1 |
| Moon     |   | 3 |   |   | 2 |   | 3 |
| Prepare  | 2 |   | 2 |   |   | 5 | 3 |
| Prize    |   |   | 1 |   | 1 |   | 2 |
| Duck     |   | 1 |   | 1 |   |   | 4 |
| Leaf     | 1 |   |   | 2 |   | 1 | 3 |

In this example, the total number of times each item was recalled was lower than in the normal aged individual of Table 5. In addition, recall of an item on one trial hardly ever resulted in recall of that item on the next trial. Thus, recall without presentation was strongly reduced in the aged individual with AD and vascular dementia. Initial recall was also reduced. Finally, this example also shows that loss of primacy in AD occurs across trials as well as within trials.

C. Methods for Scoring Itemized Recall Across Trials

Table 1 above provides codes for identifying and describing the status of itemized recall across trials, with or without presentation by selective reminding, restrictive reminding and for all recall with presentation (standard multi-trial free recall tests). These simple, empirically based designations are sufficient to identify and describe the four possible recall states in recalling a specific item across successive trials. For both standard multi-trial free recall tests with presentation of all items on all trials, selective reminding in which only those items not recalled on the preceding trial are presented before the next trial, and restricted reminding, these recall states are defined by (1) whether the recalled item was or was not recalled on the preceding trial, and (2) whether the recalled item was or was not recalled on the next trial. Although recall states in selective reminding or restricted reminding are also characterized by whether the item was recalled with or without presentation, attributes (1) and (2) are sufficient to define itemized recall states either when recall always occurs after presentation or when recall occurs with or without presentation in selective or restrictive reminding, as shown in Table 1.

The following individual protocol examples illustrate the scoring, aggregation, and analysis of itemized recall across trials, using selective reminding. The same method would also apply to itemized recall analyses of standard multi-trial recall, in which all items are presented on all trials, or to itemized recall analyses using restricted reminding, where the subject is reminded only until the item is recalled for the first time. The first example (Table 7) analyses itemized recall across trial by a healthy aged individual, the second example (Table 8) analyses recall by an aged individual with AD, and the last four examples (Tables 9–14) analyse changing recall by an aged individual who developed AD over a period of 10 years.

The upper portion of each Table shows the trial-by-trial recall of each item by a recall state number in cells where recall occurred. The numbers represent the recall state number for each item of each trial, as shown in Table 6. Shading shows recall without presentation on that trial. The last trial (T6) cannot be included in this analysis, because a non-existent additional trial is needed to determine the recall state of any items recalled on the actual last trial (T6). A next trial is always necessary to determine if items are or are not recalled on the next trial as well as on the current trial. Therefore, in the absence of a subsequent trial, the recall state of T6 cannot be assigned.

Conventional unit scoring (number of items recalled) is included, as well as the itemized recall scoring (i.e., the number of times each recall state was achieved for each item) and aggregation of the item-specific scores (Itemized score, or Iscore). In these examples, the Iscore is the numerical total of all of the recall state numbers in each trial, although the Iscore in any particular memory test of the present invention will rely on what weighting is being used. The 12-item recall list is divided into groups of four to distinguish primacy (the first four items) and recency (the last four items), as defined by the original order of presentation. While the example shown assigns values between 1 and 4 to the Recall States, the actual numerical values assigned may be other than those shown, as appropriate.

The Table is next organized to show Recall States, Scores, and Stages of item learning on each trial. Recall States shows the number of times each recall state occurred on each trial and the total number of times each recall state occurred across all 5 trials ("$\Sigma_{T1-T5}$") Non-Presentation Recall ("NPR") is the sum of the number of Recall States 3 and 4, and indicates the total number of occurrences of recall without presentation, i.e., recall from long term storage. The $\Sigma$NPR is the aggregate of the number of Recall States 3 and 4 over all 5 trials. Scores shows the Iscores on each trial and the unit scores (number of items recalled), as well as total Iscores and unit scores across all 5 trials. The ratio of Iscores to unit scores is shown by dividing the total Iscore by the total unit scores to provide a measure of the average recall state.

Finally, the Table shows Stages, which are First Recall, Learning, and Retention. First Recall is the number of items recalled for the first time. First Recall is shown as the number of items recalled for the first time, the cumulative number of items recalled for the first time, and the percentage of items recalled for the first time on each trial. Learning, as shown in the present example, is shown as the number of items recalled with presentation which resulted in recall on the next trial without presentation, and the percent of those items recalled on each trial. Retention, as shown in the present example, is the number of same items recalled without presentation which were also recalled on the next trial without presentation (Recall State 4), and is also expressed as the percentage of the total number of items recalled without presentation.

Delayed recall is conventionally estimated by comparing the number of items recalled in delayed recall with the number of items recalled on the last trial of recall before the delay. However, such delayed recall often includes 'new' items which were not recalled on the preceding trial of undelayed recall. Recall of these items does not reflect retention from the preceding trial, since they were not recalled on the previous trial. Conventional delayed recall also may be affected by the failure to recall 'new' items from the previous trial of undelayed recall. These items add noise to the estimation of retention in delayed recall. In addition, they are irrelevant to the assessment of retention from one trial to the next of undelayed recall in multi-trial learning. Therefore, "delayed retention" of the same item should present a more accurate assessment of retention after delay than conventional delayed recall.

Furthermore, retention from one trial to the next should be assessed by comparing subsequent retention with preceding retention not only in measuring delayed recall, but also in measuring trial-to-trial recall during multi-trial learning. The issue in assessing learning across trials is not the increasing number of items recalled on successive trials of learning, but the increasing number of items retained from one trial to the next. Increasing recall across trials is due to the increasing number of those items which are recalled on both trials of each pair of successive trials, but this measure is not sufficient for estimating retention. Recall of an item across at least three consecutive trials is required to show retention of that same item from one trial to the next. Therefore, retention of items recalled on the previous trial (as shown by repeated recall of the same items), not just the number of items recalled on each trial, should be regarded as the appropriate measure of learning across trials because such 'inter-trial' retention is what accounts for learning.

TABLE 7

Healthy-Aged Individual

|  | T1 | T2 | T3 | T4 | T5 | T6 | 1's | 2's | 3's | 4's | # items | Iscore | | |
|---|---|---|---|---|---|---|---|---|---|---|---|---|---|---|
| Bowl | 2 | 4 | 4 | 4 | 4 | 4 |  | 1 |  | 4 | 5 |  | 18 | |
| Passion |  | 1 |  | 2 | 4 | 4 | 1 | 1 |  | 4 | 3 | 15 | 7 | 45 |
| Dawn |  | 1 |  | 1 |  | † | 2 |  |  |  | 2 |  | 2 | |
| Judgement | 2 | 4 | 4 | 4 | 4 | 4 |  | 1 |  | 4 | 5 |  | 18 | |
| Grant |  | 2 | 4 | 4 | 4 | 4 |  | 1 |  | 3 | 4 |  | 14 | |
| Bee | 2 | 4 | 4 | 4 | 4 | 4 |  |  | 1 |  | 4 | 5 | 14 | 18 | 41 |
| Plane |  | 1 |  | 1 |  | † | 2 |  |  |  | 2 |  | 2 | |
| County |  | 1 |  | 2 | 4 | 4 | 1 | 1 |  | 4 | 3 |  | 7 | |
| Choice | 2 | 4 | 4 | 4 |  | † |  | 1 | 1 | 2 | 4 |  | 13 | |
| Seed | 2 | 4 | 4 | 4 | 4 | 4 |  | 1 |  | 4 | 5 | 16 | 18 | 45 |
| Wool | 1 |  | 1 |  | 2 | 4 | 2 | 1 |  |  | 3 |  | 4 | |
| Meal | 2 | 4 |  | 2 | 4 | 4 |  | 2 |  | 2 | 4 |  | 10 | |

† - recalled, but no subsequent trial - recall state number assignment impossible.

RECALL STATES

|  | T1 | T2 | T3 | T4 | T5 | $\Sigma_{T1-T5}$ |
|---|---|---|---|---|---|---|
| One | 1 | 4 | 1 | 2 |  | 8 |
| Two | 6 | 1 |  | 3 | 1 | 11 |
| Three | - | 1 |  | 1 | 1 | 1 |
| Four | - | 5 | 6 | 5 | 7 | 23 |

| NPR ($\Sigma(3+4)$) | - | 6 | 6 | 6 | 8 | $\Sigma$ NPR = 26 |
|---|---|---|---|---|---|---|

SCORES

| Iscore | 13 | 29 | 25 | 31 | 33 | $\Sigma$ Iscore = 131 | |
|---|---|---|---|---|---|---|---|
| # items | 7 | 11 | 7 | 11 | 9 | $\Sigma$ # items = 45 | 131/45 = 2.91 |

STAGES
1$^{ST}$ RECALL

|  | T1 | T2 | T3 | T4 | T5 |
|---|---|---|---|---|---|
| 1$^{ST}$ Recall | 7 | 5 | – | – | – |
| cumul. 1$^{ST}$/12 | 7 | 12 | 12 | 12 | 12 |
| % (cumul./12) | 0.6 | 1 | 1 | 1 | 1 |

TABLE 7-continued

Healthy-Aged Individual

LEARNING

|       | T1  | T2  | T3 | T4  | T5 | $\Sigma_{T1-T5}$ |
|-------|-----|-----|----|-----|----|------|
| 2     | 6   | 1   | 0  | 3   | 1  | 11   |
| 1 + 2 | 7   | 5   | 1  | 5   | 1  | 19   |
| %     | 0.9 | 0.2 | 0  | 0.5 | 1  | 0.58 |

RETENTION

|       | T1 | T2  | T3 | T4  | T5  | $\Sigma_{T1-T5}$ |
|-------|----|-----|----|-----|-----|------|
| 4     | –  | 5   | 6  | 5   | 7   | 23   |
| 3 + 4 | –  | 6   | 6  | 6   | 8   | 26   |
| %     | –  | 0.8 | 1  | 0.8 | 0.9 | 0.88 |

TABLE 8

Aged Individual with AD and Vascular Dementia

|         | T1 | T2 | T3 | T4 | T5 | T6 | 1's | 2's | 3's | 4's | # items | | Iscore | |
|---------|----|----|----|----|----|----|-----|-----|-----|-----|---------|---|--------|---|
| Shine   |    |    |    |    |    |    |     |     |     |     | 0       |   | 0      |   |
| Disagree|    |    |    |    |    |    |     |     |     |     | 0       | 0 | 0      | 0 |
| Fat     |    |    |    |    |    |    |     |     |     |     | 0       |   | 0      |   |
| Wealthy |    |    |    |    | †  |    |     |     |     |     | 0       |   | 0      |   |
| Drunk   |    |    |    |    |    |    |     |     |     |     | 0       |   | 0      |   |
| Pin     |    | 1  |    | 1  | †  |    | 2   |     |     |     | 2       | 6 | 2      | 9 |
| Grass   | 1  |    |    |    |    |    | 1   |     |     |     | 1       |   | 1      |   |
| Moon    |    | 2  | 3  |    | 1  |    | 1   | 1   | 1   |     | 3       |   | 6      |   |
| Prepare | 1  |    |    |    | †  |    | 2   |     |     |     | 2       |   | 2      |   |
| Prize   |    |    | 1  |    | 1  |    | 2   |     |     |     | 2       | 9 | 2      | 13|
| Duck    |    | 1  |    | 2  | 4  | †  | 1   | 1   |     | 1   | 3       |   | 7      |   |
| Leaf    | 1  |    |    | 1  | †  |    | 2   |     |     |     | 2       |   | 2      |   |

† - recalled, but no subsequent trial - recall state number assignment impossible.

RECALL STATES

|       | T1 | T2 | T3 | T4 | T5 | $\Sigma_{T1-T5}$ |
|-------|----|----|----|----|----|------|
| One   | 3  | 2  | 2  | 2  | 2  | 11   |
| Two   |    | 1  |    | 1  |    | 2    |
| Three | –  |    | 1  |    |    | 1    |
| Four  | –  |    |    |    | 1  | 1    |

| NPR ($\Sigma(3 + 4)$) | – |  | 1 |  | 1 | $\Sigma$ NPR = 2 |
|---|---|---|---|---|---|---|

SCORES

| Iscore  | 3 | 4 | 5 | 4 | 6 | $\Sigma$ Iscore = 22 | |
|---------|---|---|---|---|---|------|---|
| # items | 3 | 3 | 4 | 3 | 3 | $\Sigma$ # items = 16 | 22/16 = 1.38 |

TABLE 8-continued

Aged Individual with AD and Vascular Dementia

STAGES
1$^{ST}$ RECALL

|  | T1 | T2 | T3 | T4 | T5 |
|---|---|---|---|---|---|
| 1$^{ST}$ Recall | 3 | 3 | 1 | 0 | 0 |
| cumul. 1$^{ST}$/12 | 3 | 6 | 7 | 7 | 7 |
| % (cumul./12) | 0.25 | 0.5 | 0.58 | 0.58 | 0.6 |

LEARNING

|  | T1 | T2 | T3 | T4 | T5 | $\Sigma_{T1-T5}$ |
|---|---|---|---|---|---|---|
| 2 | 0 | 1 | 0 | 1 | 0 | 2 |
| 1 + 2 | 3 | 3 | 2 | 3 | 2 | 13 |
| % | 0 | 0.3 | 0 | 0.3 | 0 | 0.15 |

RETENTION

|  | T1 | T2 | T3 | T4 | T5 | $\Sigma_{T1-T5}$ |
|---|---|---|---|---|---|---|
| 4 | – | 0 | 0 | 0 | 1 | 1 |
| 3 + 4 | – | 0 | 1 | 0 | 1 | 2 |
| % | – | 0 | 0 | 0 | 1 | 0.5 |

TABLE 9

Aged who later developed Alzheimer's disease: 1983 (#1 of 4)

|  | T1 | T2 | T3 | T4 | T5 | T6 | 1's | 2's | 3's | 4's | # items | | Iscore | |
|---|---|---|---|---|---|---|---|---|---|---|---|---|---|---|
| Bowl |  | 2 | 4 | 4 | 4 | † |  | 1 |  | 3 | 4 |  | 14 |  |
| Passion | 2 | 3 |  | 2 | 3 |  |  | 2 | 2 |  | 4 | 13 | 10 | 33 |
| Dawn |  | 1 |  | 1 |  | † | 2 |  |  |  | 2 |  | 2 |  |
| Judgement |  | 2 | 3 |  | 2 | † |  | 2 | 1 |  | 3 |  | 7 |  |
| Grant | 2 | 4 | 3 |  | 1 |  | 1 | 1 | 1 | 1 | 4 |  | 10 |  |
| Bee |  | 1 |  | 1 |  | † | 2 |  |  |  | 2 | 13 | 2 | 32 |
| Plane | 2 | 4 | 4 | 4 | 4 | † |  | 1 |  | 4 | 5 |  | 18 |  |
| County |  | 1 |  | 1 |  | † | 2 |  |  |  | 2 |  | 2 |  |
| Choice | 2 | 4 | 4 | 3 |  | † |  | 1 | 1 | 2 | 4 |  | 13 |  |
| Seed | 2 | 4 | 4 | 4 | 4 | † |  | 1 |  | 4 | 5 | 17 | 18 | 52 |
| Wool | 1 |  | 1 |  | 1 |  | 3 |  |  |  | 3 |  | 3 |  |
| Meal | 2 | 4 | 4 | 4 | 4 | † |  | 1 |  | 4 | 5 |  | 18 |  |

† - recalled, but no subsequent trial - recall state number assignment impossible.
RECALL STATES

|  | T1 | T2 | T3 | T4 | T5 | $\Sigma_{T1-T5}$ |
|---|---|---|---|---|---|---|
| One | 1 | 3 | 1 | 3 | 2 | 10 |
| Two | 6 | 2 |  | 1 | 1 | 10 |
| Three | – | 1 | 2 | 1 | 1 | 5 |
| Four | – | 5 | 5 | 4 | 4 | 18 |

| NPR ($\Sigma(3+4)$) | – | 6 | 7 | 5 | 5 | $\Sigma$ NPR = 23 |
|---|---|---|---|---|---|---|

TABLE 9-continued

Aged who later developed Alzheimer's disease: 1983 (#1 of 4)

SCORES

| Iscore | 13 | 30 | 27 | 24 | 23 |
|---|---|---|---|---|---|
| # items | 7 | 11 | 8 | 9 | 8 |

| Σ Iscore = 117 | |
|---|---|
| Σ # items = | 117/43 = 2.72 |

STAGES
1<sup>ST</sup> RECALL

|  | T1 | T2 | T3 | T4 | T5 |
|---|---|---|---|---|---|
| 1<sup>ST</sup> Recall | 7 | 5 | – | – | – |
| cumul. 1<sup>ST</sup>/12 | 7 | 12 | 12 | 12 | 12 |
| % (cumul./12) | 0.58 | 1 | 1 | 1 | 1 |

LEARNING

|  | T1 | T2 | T3 | T4 | T5 | $\Sigma_{T1\text{-}T5}$ |
|---|---|---|---|---|---|---|
| 2 | 6 | 2 | 0 | 1 | 1 | 10 |
| 1 + 2 | 7 | 5 | 1 | 4 | 3 | 20 |
| % | 0.9 | 0.4 | 0 | 0.3 | 0.3 | 0.5 |

RETENTION

|  | T1 | T2 | T3 | T4 | T5 | $\Sigma_{T1\text{-}T5}$ |
|---|---|---|---|---|---|---|
| 4 | – | 5 | 5 | 4 | 4 | 18 |
| 3 + 4 | – | 6 | 7 | 5 | 5 | 23 |
| % | – | 0.8 | 0.7 | 0.8 | 0.9 | 0.78 |

TABLE 10

Aged who later developed Alzheimer's disease: 1989 (#2 of 4)

|  | T1 | T2 | T3 | T4 | T5 | T6 | 1's | 2's | 3's | 4's | # items | | Iscore | |
|---|---|---|---|---|---|---|---|---|---|---|---|---|---|---|
| Source | 1 |  | 2 | 4 | 4 | † | 1 | 1 |  | 2 | 4 | 15 | 11 | 49 |
| Darling |  |  | 2 | 4 | 4 | † |  | 1 |  | 2 | 4 |  | 10 |  |
| Sink |  | 2 | 4 | 4 | 4 | † |  | 1 |  | 3 | 3 |  | 14 |  |
| Boldness |  | 2 | 4 | 4 | 4 | † |  | 1 |  | 3 | 4 |  | 14 |  |
| Rib | 2 | 3 |  | 2 | 4 | † |  | 2 | 1 | 1 | 4 | 11 | 11 | 24 |
| Hook |  |  | 1 |  | † |  | 2 |  |  |  | 2 |  | 2 |  |
| Child | 2 | 3 |  | 1 |  | † | 1 | 1 | 1 |  | 3 |  | 6 |  |
| Echo |  | 1 |  | 1 |  | † | 2 |  |  |  | 2 |  | 2 |  |
| Pine |  |  | 1 |  | 1 |  | 2 |  |  |  | 2 | 11 | 2 | 23 |
| Dish |  | 1 |  | 2 | 3 |  | 1 | 1 | 1 |  | 3 |  | 6 |  |
| Chain |  | 1 |  | 1 |  | † | 2 |  |  |  | 2 |  | 2 |  |
| Rice | 2 | 4 | 4 | 3 |  | † |  | 1 | 1 | 2 | 4 |  | 13 |  |

† - recalled, but no subsequent trial - recall state number assignment impossible.

TABLE 10-continued

Aged who later developed Alzheimer's disease: 1989 (#2 of 4)

RECALL STATES

|       | T1 | T2 | T3 | T4 | T5 |     |
|-------|----|----|----|----|----|----|
| One   | 1  | 3  | 2  | 3  | 2  | 11 |
| Two   | 3  | 2  | 2  | 2  |    | 9  |
| Three | –  | 2  |    | 1  | 1  | 4  |
| Four  | –  | 1  | 3  | 4  | 5  | 13 |

| NPR | – | 3 | 3 | 5 | 6 | Σ NPR = 17 |

SCORES

| Iscore  | 7 | 17 | 18 | 26 | 25 | Σ Iscore = 93 |              |
|---------|---|----|----|----|----|---------------|--------------|
| # items | 4 | 8  | 7  | 10 | 8  | Σ # items = 37 | 93/37 = 2.51 |

STAGES
$1^{ST}$ RECALL

|                  | T1  | T2  | T3 | T4 | T5 |
|------------------|-----|-----|----|----|----|
| $1^{ST}$ Recall  | 4   | 5   | 3  | –  | –  |
| cumul. $1^{ST}$/12 | 4 | 9   | 12 | 12 | 12 |
| % (cumul./12)    | 0.3 | 0.8 | 1  | 1  | 1  |

LEARNING

|       | T1  | T2  | T3  | T4  | T5 | $\Sigma_{T1\text{-}T5}$ |
|-------|-----|-----|-----|-----|----|------|
| 2     | 2   | 3   | 2   | 2   | 2  | 0 | 9 |
| 1 + 2 | 4   | 5   | 4   | 5   | 2  | 20 |
| %     | 0.8 | 0.4 | 0.5 | 0.4 | 0  | 0.45 |

*Note: row "2" reads — 2 | 3 | 2 | 2 | 2 | 0 | 9*

RETENTION

|       | T1 | T2  | T3 | T4  | T5  | $\Sigma_{T1\text{-}T5}$ |
|-------|----|-----|----|-----|-----|------|
| 4     | –  | 1   | 3  | 4   | 5   | 13   |
| 3 + 4 | –  | 3   | 3  | 5   | 6   | 17   |
| %     | –  | 0.3 | 1  | 0.8 | 0.8 | 0.76 |

TABLE 11

Aged who later developed Alzheimer's disease: 1993 (#3 of 4)

| | T1 | T2 | T3 | T4 | T5 | T6 | | 1's | 2's | 3's | 4's | | # items | | Iscore | |
|---|---|---|---|---|---|---|---|---|---|---|---|---|---|---|---|---|
| Throw | 1 | | | | 1 | | | 2 | | | | | 2 | | 2 | |
| Lily | 2 | 4 | 4 | | 2 | 1 | | | 2 | 1 | 1 | | 4 | 12 | 11 | 31 |
| Film | | 1 | | | | † | | 1 | | | | | 1 | | 1 | |
| Discreet | 2 | 4 | 4 | 4 | 3 | | | | | 1 | 1 | 3 | 5 | | 17 | |
| Loft | | 1 | | 2 | 3 | | | 1 | 1 | 1 | | | 3 | | 6 | |
| Beef | | | 1 | | | | | 1 | | | | | 1 | 6 | 1 | 9 |
| Street | | | | | † | | | | | | | | | | | |
| Helmet | | 1 | | 1 | | † | | 2 | | | | | 2 | | 2 | |
| Snake | | | 1 | | | | | 1 | | | | | 1 | | 1 | |
| Dug | | 1 | | 1 | | † | | 2 | | | | | 2 | 9 | 2 | 9 |
| Pack | 1 | | 1 | | 1 | | | 3 | | | | | 3 | | 3 | |
| Tin | 1 | | 1 | | 1 | | | 3 | | | | | 3 | | 3 | |

† - recalled, but no subsequent trial - recall state number assignment impossible.

RECALL STATES

| | T1 | T2 | T3 | T4 | T5 | |
|---|---|---|---|---|---|---|
| One | 3 | 4 | 4 | 2 | 3 | 16 |
| Two | 2 | | | 1 | 1 | 4 |
| Three | – | | 1 | | 2 | 3 |
| Four | – | 2 | 1 | 1 | | 4 |

| NPR | – | 2 | 2 | 1 | 2 | Σ NPR = 7 |
|---|---|---|---|---|---|---|

SCORES

| Iscore | 7 | 12 | 11 | 8 | 11 | Σ Iscore = 49 | |
|---|---|---|---|---|---|---|---|
| # items | 5 | 6 | 6 | 4 | 6 | Σ # items = 27 | 49/27 = 1.81 |

STAGES
1$^{ST}$ RECALL

| | T1 | T2 | T3 | T4 | T5 |
|---|---|---|---|---|---|
| 1$^{ST}$ Recall | 5 | 4 | 2 | 0 | 0 |
| cumul. 1$^{ST}$/12 | 5 | 9 | 11 | 11 | 11 |
| % (cumul./12) | 0.42 | 0.8 | 0.9 | 0.9 | 0.92 |

LEARNING

| | T1 | T2 | T3 | T4 | T5 | Σ$_{T1-T5}$ |
|---|---|---|---|---|---|---|
| 2 | 2 | 0 | 0 | 1 | 1 | 4 |
| 1 + 2 | 5 | 4 | 4 | 3 | 4 | 20 |
| % | 0.4 | 0 | 0 | 0.3 | 0.3 | 0.25 |

RETENTION

| | T1 | T2 | T3 | T4 | T5 | Σ$_{T1-T5}$ |
|---|---|---|---|---|---|---|
| 4 | – | 2 | 1 | 1 | 0 | 4 |
| 3 + 4 | – | 2 | 2 | 1 | 2 | 7 |
| % | – | 1 | 0.5 | 1 | 0 | 0.57 |

TABLE 12

Aged who later developed Alzheimer's disease: 1994 (#4 of 4)

| | T1 | T2 | T3 | T4 | T5 | T6 | 1's | 2's | 3's | 4's | # items | Iscore | | |
|---|---|---|---|---|---|---|---|---|---|---|---|---|---|---|
| Bowl | | | | 1 | | | 1 | | | | 1 | 1 | | |
| Passion | 1 | | | 2 | † | | 1 | 1 | | | 2 | 3 | 3 | 4 |
| Dawn | | | | | | | | | | | | | | |
| Judgement | | | | | | | | | | | | | | |
| Grant | | | | | | | | | | | | | | |
| Bee | | | | | | | | | | | 2 | | | 2 |
| Plane | | | 1 | | | | 1 | | | | 1 | 1 | | |
| County | | | | 1 | | | 1 | | | | 1 | 1 | | |
| Choice | | | 1 | | 1 | | 2 | | | | 2 | 2 | | |
| Seed | | 1 | | 1 | | | 2 | | | | 2 | 11 | 2 | 24 |
| Wool | | | 1 | | 1 | | 2 | | | | 2 | 2 | | |
| Meal | 2 | † | † | † | † | † | | | 1 | | 5 | 18 | | |

† - recalled, but no subsequent trial - recall state number assignment impossible.

RECALL STATES

| | T1 | T2 | T3 | T4 | T5 | |
|---|---|---|---|---|---|---|
| One | | 1 | 12 | 3 | 3 | 10 |
| Two | 1 | | | | 1 | 2 |
| Three | – | | | | | |
| Four | – | 1 | 1 | 1 | 1 | 4 |

| NPR | – | 1 | 1 | 1 | 1 | Σ NPR = 4 |
|---|---|---|---|---|---|---|

SCORES

| Iscore | 3 | 5 | 6 | 7 | 9 | Σ Iscore = 30 | |
|---|---|---|---|---|---|---|---|
| # items | 2 | 2 | 3 | 4 | 5 | Σ # items = 16 | 30/16 = 1.88 |

STAGES
$1^{ST}$ RECALL

| | T1 | T2 | T3 | T4 | T5 |
|---|---|---|---|---|---|
| $1^{ST}$ Recall | 2 | 1 | 2 | 2 | 1 |
| cumul. $1^{ST}$/12 | 2 | 3 | 5 | 7 | 8 |
| % (cumul./12) | 0.2 | 0.3 | 0.42 | 0.58 | 0.7 |

LEARNING

| | T1 | T2 | T3 | T4 | T5 | $\Sigma_{T1-T5}$ |
|---|---|---|---|---|---|---|
| 2 | 1 | 0 | 0 | 0 | 1 | 2 |
| 1 + 2 | 2 | 1 | 2 | 3 | 4 | 12 |
| % | 0.5 | 0 | 0 | 0 | 0.3 | 0.17 |

RETENTION

| | T1 | T2 | T3 | T4 | T5 | $\Sigma_{T1-T5}$ |
|---|---|---|---|---|---|---|
| 4 | – | 1 | 1 | 1 | 1 | 4 |
| 3 + 4 | – | 1 | 1 | 1 | 1 | 4 |
| % | – | 1 | 1 | 1 | 1 | 1 |

The most striking change in the parameters measured is in the values for the sum of the Iscores and the sum of the NPR. In the case of the healthy aged individual, the Σ Iscore was 131, and the Σ NPR was 26 (Table 7). By comparison, the aged individual with AD and vascular dementia had an Σ Iscore of 22 (17% of that of the healthy individual) and an Σ NPR score of 2 (7% of that of the healthy individual) (Table 8). The aged individual who later developed AD started with scores only slightly different from those of the healthy aged individual (Σ Iscore=117 vs. 131; Σ NPR=23 vs. 26) (compare Tables 7 and 9). However, eleven years later this individual had scores similar to those of the aged individual with AD and vascular dementia (Σ Iscore=30 vs. 22; Σ NPR=4 vs. 2) (compare Tables 8 and 12). Significant declines were also evident in the $1^{st}$ Recall and Learning Stages, indicating a loss of the ability of recall items from STS.

With respect to the $1^{st}$ Recall Stage, it is also evident that the number of presentations required to elicit the first recall of each item appears to provide an estimate of the subject's ability to remember and learn. In Table 7, it can be seen that in the First Recall stage, all the items were recalled for the first time by Trial 2. In contrast, in Table 8, it can be seen that some of the items were never recalled at all. Similarly, by following the first recall of items in Tables 9–12, showing the progressive decline of the same individual over time, it can be seen that a progressively greater number of trials was required for first recall of all the items. In Table 11, 10 years after the first measurements were taken, 11 of 12 items were recalled at least once, and in Table 12, 11 years after the first measurement, only 8 of 12 items were recalled at all. Therefore, the number of presentations required to elicit the first recall of the items may provide a useful estimate of item-specific memory and learning across trials.

It is possible to include RWR on each trial of multi-trial recall protocols, or to include a combination of RWR and weighting across trials, as appropriate. Furthermore, the RWR analysis may be extended from a single trial across multiple trials and the results aggregated, as appropriate. The weighting across trials may be performed with or without controlled reminding, and may further include steps of free or cued recall.

The number of presentations required to elicit the first recall of each item may also be presented in a visual format. For example, Tables 13–16 show the progressively increasing number of presentations needed to elicit the first recall of each item by an aged individual who developed AD over a period of 10 years. The shaded cells indicate the trials on which the items were presented until items were recalled for the first time. The numbers in cells indicate recall states. The first number (left) in each row indicates the first recall of that item. A "1" indicates the item was not recalled on the next trial, a "2" indicates the item was recalled on the next trial without presentation (showing learning). The last column (right) shows the number of presentations needed to elicit the first recall ($1^{st}$ recall) of each item, and the total number of presentations needed to elicit the first recall of the first 4 items (primacy). the second 4 items, and the last 4 items (recency).

TABLE 13

1983

|  | T1 | T2 | T3 | T4 | T5 | presentations to $1^{st}$ recall | |
|---|---|---|---|---|---|---|---|
| Bowl |  |  | 4 | 4 | 4 | 2 | |
| Passion |  | 2 |  | 2 | 2 | 1 | 7 |
| Dawn |  |  |  | 1 |  | 2 | |
| Judgement |  |  | 3 |  | 2 | 2 | |
| Grant |  | 4 | 3 |  | 1 | 1 | |
| Bee |  |  |  | 1 |  | 2 | 6 |
| Plane |  | 4 | 4 | 4 | 4 | 1 | |
| County |  |  |  | 1 |  | 2 | |
| Choice |  | 4 | 4 | 3 |  | 1 | |
| Seed |  | 4 | 4 | 4 | 4 | 1 | 4 |
| Wool |  |  | 1 |  | 1 | 1 | |
| Meal |  | 4 | 4 | 4 | 4 | 1 | |
| presentations | 12 | 5 |  |  |  | 17 | |
| cumulative | 12 | 17 |  |  |  |  | |
| $1^{st}$ recall | 7 | 5 |  |  |  | 17/12= 1.4 | |
| cumulative | 7 | 12 |  |  |  |  | |
| 2 | 6 | 2 |  |  |  | 8/12 = .67 | |
| 1+2 | 7 | 5 |  |  |  | | |

TABLE 14

1989

|  | T1 | T2 | T3 | T4 | T5 | presentations to $1^{st}$ recall | |
|---|---|---|---|---|---|---|---|
| Source |  |  | 2 | 4 | 4 | 1 | |
| Darling |  |  |  | 4 | 4 | 3 | 8 |
| Sink |  |  | 4 | 4 | 4 | 2 | |
| Boldness |  |  | 4 | 4 | 4 | 2 | |
| Rib |  | 3 |  | 2 | 4 | 1 | |
| Hook |  |  |  |  | 1 | 3 | 7 |
| Child |  | 3 |  | 1 |  | 1 | |
| Echo |  |  |  | 1 |  | 2 | |
| Pine |  |  |  |  | 1 | 3 | |
| Dish |  |  |  |  | 3 | 2 | 8 |
| Chain |  |  |  |  |  | 2 | |
| Rice |  | 4 | 4 |  |  | 1 | |
| presentations | 12 | 8 | 3 |  |  | 23 | |
| cumulative | 12 | 20 | 23 |  |  |  | |
| $1^{st}$ recall | 4 | 5 | 3 |  |  | 23/12= 1.9 | |
| Cumulative | 4 | 9 | 12 |  |  |  | |
| 2 | 3 | 2 | 1 |  |  | 6/12 = .50 | |
| 1 + 2 | 4 | 5 | 3 |  |  |  | |

TABLE 15

1993

| | T1 | T2 | T3 | T4 | T5 | presentations to 1st recall | |
|---|---|---|---|---|---|---|---|
| Throw | 1 | | | 1 | 1 | | |
| Lily | 2 | 4 | 3 | | 2 | 1 | 5 |
| Film | 1 | | | | | 2 | |
| Discreet | 2 | 4 | 4 | 4 | 3 | 1 | |
| Loft | | 1 | | 2 | 3 | 2 | |
| Beef | | | 1 | | | 3 | 12 |
| Street | | | | | | 5 | |
| Helmet | | 1 | | 1 | | 2 | |
| Snake | | | 1 | | | 3 | |
| Dug | | 1 | | 1 | | 2 | 7 |
| Pack | 1 | | 1 | | 1 | 1 | |
| Tin | 1 | | 1 | | 1 | 1 | |
| presentations | 12 | 7 | 3 | 1 | 1 | 24 | |
| cumulative | 12 | 19 | 22 | 23 | 24 | | |
| 1st recall | 5 | 4 | 2 | 0 | 0 | 24/11= 2.2 | |
| cumulative | 5 | 9 | 11 | 11 | 11 | | |
| 2 | 2 | 0 | 0 | | | 2/11 = .18 | |
| 1 + 2 | 5 | 4 | 2 | | | | |

TABLE 16

1994

| | T1 | T2 | T3 | T4 | T5 | presentations to 1st recall | |
|---|---|---|---|---|---|---|---|
| Bowl | | | | | 1 | 5 | |
| Passion | 1 | | | | 2 | 1 | 16 |
| Dawn | | | | | | 5 | |
| Judgement | | | | | | 5 | |
| Grant | | | | | | 5 | |
| Bee | | | | | | 5 | 18 |
| Plane | | | | 1 | | 4 | |
| County | | | | 1 | | 4 | |
| Choice | | | 1 | | 1 | 3 | |
| Seed | | 1 | | 1 | | 2 | 9 |
| Wool | 2 | | 1 | | 1 | 3 | |
| Meal | | 4 | 4 | 4 | 4 | 1 | |
| presentations | 12 | 10 | 3 | 7 | 5 | 43 | |
| cumulative | 12 | 22 | 31 | 38 | 43 | | |
| 1st recall | 2 | 1 | 2 | 2 | 1 | 43/8 = 5.4 | |
| cumulative | 2 | 3 | 5 | 7 | 8 | | |
| 2 | 12 | 0 | 0 | 0 | 0 | 1/8 = .125 | |
| 1 + 2 | 2 | 1 | 2 | 2 | 1 | | |

In Table 13, first recall of all items occurred by Trial 2 (T2). Table 14 shows the beginning of the progressive decline in first recall, with 3 items not recalled until Trial 3 (T3) and 8 items not recalled until T2. In Table 15, one item was not recalled for at least 5 trials, 2 items were not recalled until T3, and 4 items not recalled until T2. In Table 16, 4 items were not recalled for at least 5 trials, 1 item was not recalled until T5, 2 items were not recalled until T4, two items were not recalled until T3, and one item was not recalled until T2 and the serial position distribution of the number of presentations needed to elicit first recall shows loss of primacy consistent with Alzheimer's Disease. The serial position effects shown by the number of presentations needed to elicit the first recall of each item appears to provide a serial position curve for an individual (over trials) helping to show in an individual the loss of primacy seen in the serial position curves that can otherwise be obtained only from a group of individuals.

Tables 13–16 show that the number of presentations needed to elicit $1^{st}$ recall increased from 17 to 23 to 24 to 43 (when AD was diagnosed). The mean number of presentations per item increased from 1.4 to 1.9 to 2.2 to 5.4. Tables 13 to 16 also show that the proportion of items learned on $1^{st}$ recall (recall state=2) decresed from 0.67 to 0.50 to 0.18 to 0.12 (when AD was diagnosed).

Comparison of recall states 1 and 2 for first recall in Tables 13–16 also appears to show that when first recall did not result in recall on the next trial (i.e., when first recall state=1), those items were rarely learned later; i.e., those items are subsequently recalled again only when presented again, but are not recalled without presentation.

Accordingly, while the trials above indicated a memory deficiency as shown by the increasing number of trials to reach First Recall, item-specific learning across trials can be measured by analyzing the number of trials to reach any recall state (1, 2, 3, or 4). Item-specific learning of each item can be measured by aggregating the number of trials to reach the recall state for each item. Further, the relations among the measures of such trials to reach recall states and the transitions between successive recall states can be analyzed to provide measures of item-specific learning and indicate memory impairment.

III. Methods to Prevent Ceiling Effects

As illustrated in Tables 17–20, the ceiling effects that limit interpretation of Total Recall in the standard 16-item Free & Cued Selective Reminding Test (FCSRT) can be prevented by introducing an "extended" delay (at least 2 minutes) with interference before the first recall trial. Ceiling effects occur when a significant proportion of test subjects perform so well in a memory test that distinction among the subjects is hindered. Ceiling effects in total recall (Free Recall+Cued Recall) in the FCSRT, due to the very effective cued recall elicited by controlled learning and encoding specificity in the FCSRT, limit assessment of learning, memory and retention, and the detection of limitations in recall. By overcoming ceiling effects in the FCSRT, limitations in free recall and cued recall should be more easily detected, and therefore discrimination based on total recall should also be improved and staging and tracking of memory impairment by the FCSRT may be possible. As a result, detection of changes in free, cued, and/or total recall over time may be improved.

Tables 17–20 compare performance on two separate FCSRT tests, after an extended (10 minute) delay with interference (left) and after a very brief 30 second delay with interference. "F" indicates free recall, "C" indicates cued recall, and "X" indicates an incorrect response.

Table 17 shows the performance of a non-demented aged individual on two separate FCSRT tests with extended interference delay on the left and a very brief delay on the right. The percentage of items recalled by free recall (Free Recall/16) dropped after a 10-minute delay relative to a 30-second delay (Trial 1: 0.56 to 0.06; Trial 2: 0.69 to 0.38). The percentage of items recalled by cued recall (Cued Recall/(16-Free Recall)) also dropped after the 10-minute delay relative to the 30-second delay (Trial 1: 1.00 to 0.60; Trial 2: 1.00 to 0.90). The percentage of total items recalled (Total Recall/16) also dropped after the 10-minute delay relative to the 30-second delay (Trial 1: 1.00 to 0.63; Trial 2: 1.00 to 0.94).

TABLE 17

| Category Cue | Item | 10 M Delay | Trial 1 | Trial 2 | 30 s Delay | Trial 1 | Trial 2 |
|---|---|---|---|---|---|---|---|
| Bird | Owl | | F | F | | F | C |
| Item for Carrying | Basket | | C | C | | C | F |
| Vegetable | Onion | | X | F | | F | C |
| Worn of Feet | Skates | | C | C | | F | C |
| Dessert | Cake | | X | X | | C | F |
| Smoking Item | Pipe | | C | C | | C | F |
| Jewelry | Watch | | C | C | | C | F |
| Building | Cabin | | X | F | | F | F |
| Furniture | Desk | | X | C | | C | C |
| Transportation | Train | | C | C | | F | F |
| Musical Instrument | Guitar | | C | C | | F | F |
| Kitchen Appliance | Toaster | | X | F | | F | C |
| Sports Equipment | Racquet | | X | F | | F | F |
| Plant | Cactus | | C | C | | F | F |
| Ship Part | Anchor | | C | F | | C | F |
| Free Recall | | | 1 | 6 | | 9 | 11 |
| Free Recall / 16 | | | 0.06 | 0.38 | | 0.56 | 0.69 |
| Cued Recall | | | 9 | 9 | | 7 | 5 |
| Cued Recall/(16-Free Recall) | | | 0.60 | 0.90 | | 1.00 | 1.00 |
| Free Recall + Cued Recall | | | 10 | 15 | | 16 | 16 |
| Total Recall / 16 | | | .63 | .94 | | 1.00 | 1.00 |
| Retreival Weighted Score = (2 × Free Recall) + Cued Recall | | | 11 | 21 | | 25 | 27 |
| Retreival Weighted Score /32 | | | .34 | .66 | | .78 | .84 |

Table 18 shows the results for the same test for a second non-demented aged individual. The percentage of items recalled by free recall (Free Recall/16) dropped after a 10-minute delay relative to a 30-second delay (Trial 1: 0.63 to 0.33; Trial 2: 0.88 to 0.69). The percentage of items recalled by cued recall (Cued Recall/(16-Free Recall)) also dropped after the 10-minute delay relative to the 30-second delay in the first trial, but not in the second (Trial 1: 1.00 to 0.67; Trial 2: 1.00 to 1.00). Similarly, the percentage of total items recalled was reduced after the 10 minute delay relative to the 30 second delay in the first trial, but not in the second (Trial 1: 1.00 to 0.75; Trial 2: 1.00 to 1.00).

TABLE 18

| Category Cue | Item | 10 M Delay | Trial 1 | Trial 2 | 30 s Delay | Trial 1 | Trial 2 |
|---|---|---|---|---|---|---|---|
| Insect | Spider | | C | C | | F | F |
| Seafood | Lobster | | C | C | | F | F |
| Baking | Rolling Pin | | C | C | | C | F |
| Body Part | Foot | | X | F | | C | F |
| Light Source | Candle | | F | F | | F | F |
| Liquid Holder | Pitcher | | C | C | | C | F |
| Sewing Item | Thread | | C | F | | C | F |
| Four Footed Animal | Bear | | X | F | | F | F |
| Toy | Whistle | | X | F | | F | C |
| Geometric Shape | Star | | F | F | | F | F |
| Building Part | Chimney | | F | F | | F | F |
| Cleaning Tool | Broom | | C | C | | F | C |
| Fruit | Grapes | | F | F | | C | F |
| Clothing | Vest | | C | F | | F | F |
| Worn on Head | Crown | | X | F | | F | F |
| Weapon | Sword | | C | F | | C | F |
| Free Recall | | | 4 | 11 | | 10 | 14 |
| Free Recall / 16 | | | 0.33 | 0.69 | | 0.63 | 0.88 |
| Cued Recall | | | 8 | 5 | | 6 | 2 |
| Cued Recall/(16-Free Recall) | | | 0.67 | 1.00 | | 1.00 | 1.00 |
| Free Recall + Cued Recall | | | 12 | 16 | | 16 | 16 |
| Total Recall / 16 | | | .75 | 1.00 | | 1.00 | 1.00 |
| Retreival Weighted Score = (2 × Free Recall) + Cued Recall | | | 16 | 27 | | 26 | 30 |
| Retreival Weighted Score /32 | | | .50 | 84 | | 81 | 94 |

Tables 19 and 20 show the same tests taken by two separated demented aged individuals. Free recall, cued recall, and total recall all were reduced relative to the non-demented aged (compare Tables 19 and 20 to Tables 17 and 18). As was the case with the non-demented aged subjects, the percentage of items recalled by free recall (Free Recall/16) dropped after a 10-minute delay relative to a 30-second delay (Trial 1: 0.31 to 0.00; Trial 2: 0.31 to 0.25). The percentage of items recalled by cued recall (Cued Recall/(16-Free Recall)) also dropped after the 10-minute delay relative to the 30-second delay in both individuals. Finally, the percentage of total items recalled (Total Recall/16) in both individuals also dropped after the 10-minute delay relative to the 30-second delay. The only exception is shown in Table 20, where the percentage of items recalled by cued recall rose after a 10-minute delay in Trial 2, and this rise was also reflected in the percentage of total items recalled in Trial 2. These values were much lower than the corresponding values obtained with non-demented individuals (compare to Tables 17 and 18). Thus, extended delay (10 minutes) substantially reduced cued recall and total recall as well as free recall in both non-demented and demented aged subjects, and prevents the ceiling effects that occur when no extended delay is introduced before the first recall. Total Recall after extended delay aged with dementia (Tables 19 and 20) is substantially less that Total Recall by aged without dementia (Tables 17 and 18).

It will be appreciated by those in the art that the duration of the extended delay may be shorter or longer than 10 minutes. Too long a period of extended delay will result in forgetting of the items, while too short a period of extended delay will cause loss of the discriminatory power of the extended delay. Accordingly, it would be within the skill of those in the art to optimize the period of the extended delay as required.

Tables 17 to 20 also illustrate that the selective weighting of items retrieved by free recall in memory tests utilizing free and cued recall prevents ceiling effects and increases specificity.

TABLE 19

| Category Cue | Item | 10 M Delay | Trial 1 | Trial 2 | 30 s Delay | Trial 1 | Trial 2 |
|---|---|---|---|---|---|---|---|
| Insect | Spider | | X | C | | C | C |
| Seafood | Lobster | | C | C | | C | C |
| Baking | Rolling Pin | | X | X | | C | C |
| Body Part | Foot | | X | C | | C | F |
| Light Source | Candle | | C | X | | C | C |
| Liquid Holder | Pitcher | | X | C | | C | C |
| Sewing Item | Thread | | X | C | | F | F |
| Four Footed Animal | Bear | | X | C | | F | F |
| Toy | Whistle | | X | X | | F | C |
| Geometric Shape | Star | | X | X | | F | C |
| Building Part | Chimney | | C | C | | X | X |
| Cleaning Tool | Broom | | C | C | | F | F |
| Fruit | Grapes | | C | F | | C | C |
| Clothing | Vest | | X | F | | X | C |
| Worn on Head | Crown | | X | F | | F | X |
| Weapon | Sword | | X | F | | C | F |
| Free Recall | | | 0 | 4 | | 5 | 5 |
| Free Recall/16 | | | 0 | 0.25 | | 0.31 | 0.31 |
| Cued Recall | | | 5 | 8 | | 9 | 9 |
| Cued Recall/(16-Free Recall) | | | 0.31 | 0.67 | | .82 | .82 |
| Free Recall + Cued Recall | | | 5 | 12 | | 14 | 14 |
| Total Recall / 16 | | | .31 | .75 | | .88 | .88 |
| Retreival Weighted Score = (2 × Free Recall) + Cured Recall | | | 5 | 16 | | 19 | 19 |
| Retreival Weighted Score | | | .16 | .50 | | .59 | .59 |

TABLE 20

| Category | Item | 10 M Delay | Trial 1 | Trial 2 | 30 s Delay | Trial 1 | Trial 2 |
|---|---|---|---|---|---|---|---|
| Insect | Spider | | C | C | | C | X |
| Seafood | Lobster | | X | C | | X | X |
| Baking | Rolling Pin | | X | C | | C | X |
| Body Part | Foot | | X | C | | C | C |
| Light Source | Candle | | X | C | | C | C |
| Liquid Holder | Pitcher | | X | X | | C | C |
| Sewing Item | Thread | | X | C | | C | C |
| Four Footed Animal | Bear | | X | C | | C | C |
| Toy | Whistle | | X | X | | F | F |
| Geometric Shape | Star | | X | C | | F | C |
| Building Part | Chimney | | X | C | | F | F |
| Cleaning Tool | Broom | | X | C | | F | F |
| Fruit | Grapes | | C | C | | F | C |
| Clothing | Vest | | X | X | | C | C |
| Worn on Head | Crown | | X | C | | F | X |
| Weapon | Sword | | X | X | | F | X |

TABLE 20-continued

| Category | Item | 10 M Delay Trial 1 | Trial 2 | 30 s Delay | Trial 1 | Trial 2 |
|---|---|---|---|---|---|---|
| | Free Recall | 0 | 0 | | 6 | 3 |
| | Free Recall / 16 | 0.0 | 0.00 | | 0.38 | 0.19 |
| | Cued Recall | 3 | 12 | | 9 | 8 |
| | Cued Recall/(16-Free Recall) | 0.19 | 0.75 | | 9 | .62 |
| | Free Recall + Cued Recall | 3 | 12 | | 15 | 11 |
| | Total Recall / 16 | .19 | 0.75 | | 0.94 | 0.69 |
| | Retreival Weighted Score = (2 × Free Recall) + Cued Recall | 2 | 12 | | 21 | 14 |

IV. Alzheimer's Dementia Memory Impairment Test ("ADMIT")

Some Recall States may discriminate normal aged from demented aged or aged with AD better than other Recall States. If certain Recall State(s) better discriminate such subjects, more sensitive and more specific tests can be designed to focus specifically on the recall component(s) that appear to be most important for discrimination. In addition to the previous delayed FSCRT test, a CR only can be used, or free recall alone can be used as described below.

One embodiment of an Alzheimer's Dementia Memory Impairment Test is a version of Restricted Reminding, in which each item is presented only until it has been recalled once with presentation, followed by recall (attempts) without presentation to determine what proportion of items recalled for the first time with presentation are learned for retrieval on the next trial. That is, the test determines the proportion of items recalled without presentation (after items have been recalled for the first time with presentation), i.e., the probability of learning (or encoding for retrieval without further presentation). In addition to focusing on the learning phase, this Restricted Reminding version also tests the first recall stage of First Recall (which may also be impaired in early AD), by showing the number of presentations needed to elicit the First Recall of each item. This allows the determination of the probability of initial recall with presentation. The preferred form of the test is performed with controlled learning of 16 items, and forward cued recall of all items in order of presentation. Preferably, four trials are performed, with no reminding on the last trial. Additional learning trials may be added, as desired, and conversely, only the first two trials may be performed if all that is required is to assess learning by recall without presentation on the second trial.

Tables 21 and 22 provide examples of a Free Recall ADMIT test for a normal aged subject and an aged subject with AD, respectively. In each case, each of 10 items was presented until it had been recalled once ("restricted reminding"). Presentations are indicated by shading. Recall is indicated by numbers in cells. The numbers in cells designate simplified recall stages shown by recall on the next trial (without presentation), i.e., learning: 2=recalled on the current trial and on the next trial, and 1=recalled on the current trial but not on the next trial. Item-specific Weighted Recall is the sum of recall stage numbers.

TABLE 21

Normal Aged Subject

| | Trial 1 | Trial 2 | Trial 3 | Trial 4 | Trial 5 |
|---|---|---|---|---|---|
| Happy | 1 | | | | |
| Cheap | | 2 | 1 | | |
| Smooth | | 2 | 2 | 2 | 2 |
| Noisy | 1 | | | | |
| Thin | 2 | 2 | 2 | 2 | 2 |
| Young | | 2 | 2 | 2 | 2 |
| Calm | | | 1 | | |
| Warm | | 2 | 2 | 1 | |
| Empty | | 2 | 2 | 2 | 2 |
| Strong | 1 | | | | |

| | | | | | |
|---|---|---|---|---|---|
| Recall | 4 | 10 | 17 | 22 | 26 |
| Weighted Recall | 5 | 17 | 29 | 38 | 46 |

| | | | | | |
|---|---|---|---|---|---|
| 1st Recall | 4 | 9 | 10 | 10 | 10 |
| Learning | – | 1 | 7 | 7 | 7 |
| Retention | – | – | 1 | 6 | 10 |

TABLE 22

Aged Subject with AD

| | Trial 1 | Trial 2 | Trial 3 | Trial 4 | Trial 5 |
|---|---|---|---|---|---|
| Happy | 1 | | 2 | 2 | 2 |
| Cheap | 1 | | | | |
| Smooth | | 1 | | | |
| Noisy | | | 2 | 1 | |
| Thin | | | 2 | 2 | 2 |
| Young | | 2 | 2 | 2 | 2 |
| Calm | | 1 | | | 1 |
| Warm | | | | 2 | 2 |
| Empty | 1 | 1 | | | |
| Strong | 1 | | | | |

| | | | | | |
|---|---|---|---|---|---|
| Recall | 4 | 7 | 11 | 16 | 21 |
| Weighted Recall | 4 | 8 | 16 | 25 | 34 |

| | | | | | |
|---|---|---|---|---|---|
| 1st Recall | 4 | 7 | 9 | 10 | 10 |
| Learning | – | 0 | 2 | 4 | 6 |
| Retention | – | – | 0 | 2 | 5 |

The results show that by Trial 3, the normal aged individual learned a total of 6 different items, as shown by recall without presentation (numbers in clear cells in Table 21). In contrast, the aged individual with AD learned only 2 different items by Trial 3, and did not learn 6 items until Trial 5 (Table 22). Retention is shown by recall of the same item without presentation on two successive trials. Retention scores show that on Trial 4 the normal aged individual had a total retention score of 6, but the aged individual with AD had a retention score of only 2, and that by Trial 5 the normal aged individual had a total retention score of 10, but the aged individual with AD had a total retention score of only 5. Item-Specific Weighted Recall shows that by Trial 3 the normal aged individual had a weighted recall score of 29, but the aged individual with AD had a weighted recall score of only 16, and that by Trial 5 the normal aged had a total weighted recall score of 46, but the aged individual with AD had total weighted recall score of only 34. Thus, there is a clear difference between normal aged and aged with AD in ability to learn and retain items for recall without presentation. This difference can form the basis for one or more new tests for AD.

All publications mentioned herein are incorporated by reference in their entirety. While the foregoing invention has been described in some detail for the purposes of clarity and understanding, it will be appreciated by one skilled in the art from a reading of the disclosure that various changes in form and detail can be made without departing from the true scope of the invention in the appended claims.

What is claimed is:

1. A method for measuring memory in a subject, comprising the steps of:
   (a) presenting a list of items to a subject to be recalled from memory by the subject;
   (b) recording items recalled by the subject;
   (c) assigning a non-normative weighted value to each item recalled by the subject, wherein the value for each item is weighted according to the period of retention of the item by the subject before recall; and
   (d) analyzing the assigned values of items recalled by the subject.

2. The method of claim 1, further comprising introducing an interference delay between presentation and recordation.

3. The method of claim 1, wherein the values are further weighted according to the probability of recall of that item by members of a reference group.

4. The method of claim 1, wherein the values are further weighted according to the relative difficulty of recalling the item.

5. The method of claim 1, wherein the step of analyzing the assigned values comprises calculating a score for the subject based on the weighted values and comparing the score to a reference score.

6. The method of claim 5, wherein the reference score establishes memory impairment.

7. The method of claim 6, wherein the memory impairment is indicative of dementia.

8. The method of claim 7, wherein the dementia is Alzheimer's Disease.

9. A method for measuring memory in a subject, comprising the steps of:
   (a) in a first trial, presenting a list of items to a subject to be recalled from memory by the subject;
   (b) recording items that are recalled by the subject from memory;
   (c) repeating the steps of (a) and (b) at least two more times;
   (d) assigning a non-normative weighted value to each item recalled by the subject from memory in each trial; and
   (e) analyzing the assigned values of the items recalled by the subject.

10. The method of claim 9, wherein the value of each item recalled in each trial is weighted according to whether the item has been recalled in the preceding trial or the following trial.

11. The method of claim 10, wherein the values are further weighted according to the probability of recall of that item by members of a reference group.

12. The method of claim 9, wherein the values are further weighted according to the order in which the items are presented to the subject.

13. The method of claim 9, wherein the values are further weighted according to the relative difficulty of recalling the item.

14. The method of claim 10, wherein the step of analyzing the assigned values comprises calculating a score for the subject based on the weighted values and comparing the score to a reference score.

15. The method of claim 14, wherein the reference score establishes memory impairment.

16. The method of claim 15, wherein the memory impairment indicates dementia.

17. The method of claim 16, wherein the dementia is Alzheimer's Disease.

18. A method of reducing ceiling effects in serial processing memory tests, comprising introducing an interference delay between (a) presentation of a list of items to a subject wherein said items are to be recalled from memory by the subject and (b) first recall of the items by the subject from memory, wherein each item recalled from memory by the subject is assigned a non-normative weighted value in each trial.

19. A method of reducing ceiling effects in serial processing memory tests using free and cued recall, comprising scoring the test by selectively weighting the value of each item recalled by the subject in each trial without presentation of a cue, wherein each item recalled from memory by the subject is assigned a non-normative weighted value in each trial.

* * * * *